US011819628B2

(12) United States Patent
Sakaguchi

(10) Patent No.: US 11,819,628 B2
(45) Date of Patent: *Nov. 21, 2023

(54) CATHETER HOLDER AND CATHETER SET

(71) Applicant: TERUMO KABUSHIKI KAISHA, Tokyo (JP)

(72) Inventor: Yuuki Sakaguchi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/727,865

(22) Filed: Apr. 25, 2022

(65) Prior Publication Data
US 2022/0241550 A1 Aug. 4, 2022

Related U.S. Application Data

(63) Continuation of application No. 15/609,143, filed on May 31, 2017, now Pat. No. 11,331,450, which is a
(Continued)

(30) Foreign Application Priority Data

Dec. 2, 2014 (JP) .................................. 2014-244259

(51) Int. Cl.
*A61M 25/00* (2006.01)
*A61B 8/12* (2006.01)
(Continued)

(52) U.S. Cl.
CPC ............ *A61M 25/002* (2013.01); *A61B 1/00* (2013.01); *A61B 5/0084* (2013.01); *A61B 8/12* (2013.01);
(Continued)

(58) Field of Classification Search
CPC ............ A61M 25/002; A61M 25/0097; A61M 25/0904; A61M 39/223;
(Continued)

(56) References Cited

U.S. PATENT DOCUMENTS 5,344,011 A 9/1994 Dibernardo et al.
5,366,444 A 11/1994 Martin
(Continued)

FOREIGN PATENT DOCUMENTS

EP 2474267 A1 7/2012
JP 2001505449 A 4/2001
(Continued)

OTHER PUBLICATIONS

The extended European Search Report dated Jun. 26, 2018, by the European Patent Office in corresponding European Patent Application No. 15865046.5-1124. (7 pages).
(Continued)

*Primary Examiner* — J. Gregory Pickett
*Assistant Examiner* — Jenine Pagan
(74) *Attorney, Agent, or Firm* — BUCHANAN INGERSOLL & ROONEY PC

(57) ABSTRACT

A catheter holder includes an attachment section configured to be attachable to a holder tube that accommodates at least a portion of a sheath of an image diagnosis catheter in a wound state, a support section extending from the attachment section in a direction away from the wound holder tube, and a fixing section provided on a second end side of the support section, which is opposite to a first end side of the support section on which the attachment section is provided, and configured to fix a unit connector and a hub of the image diagnosis catheter to hold the outer tube, which is exposed from an opening portion of the holder tube, in a linear shape to be fixed in position.

10 Claims, 11 Drawing Sheets

Related U.S. Application Data continuation of application No. PCT/JP2015/083804, filed on Dec. 1, 2015.

(51) Int. Cl.
　　*A61B 1/00*　　　(2006.01)
　　*A61B 5/00*　　　(2006.01)
　　*A61M 25/09*　　(2006.01)
　　*A61M 39/22*　　(2006.01)

(52) U.S. Cl.
　　CPC .. *A61M 25/0097* (2013.01); *A61M 25/09041* (2013.01); *A61M 39/223* (2013.01); *A61M 2025/09166* (2013.01); *A61M 2039/229* (2013.01)

(58) Field of Classification Search
　　CPC .. A61M 2025/09166; A61M 2039/229; A61B 5/0084; A61B 8/12
　　USPC ........................................................ 206/571
　　See application file for complete search history.

(56) References Cited

U.S. PATENT DOCUMENTS

| | | | |
|---|---|---|---|
| 5,484,419 | A | 1/1996 | Fleck |
| 5,507,300 | A | 4/1996 | Mukai et al. |
| 5,827,202 | A | 10/1998 | Miraki et al. |
| 5,843,002 | A | 12/1998 | Pecor et al. |
| 6,053,313 | A | 4/2000 | Farrell et al. |
| 7,357,787 | B2 | 4/2008 | Moss |
| 9,011,351 | B2 | 4/2015 | Hoshinouchi |
| 9,706,904 | B2 | 7/2017 | Matsuno et al. |
| 11,331,450 | B2 * | 5/2022 | Sakaguchi .......... A61M 39/223 |
| 2002/0130059 | A1 | 9/2002 | Armijo |
| 2003/0036712 | A1 | 2/2003 | Heh et al. |
| 2004/0230136 | A1 | 11/2004 | Corrigan |
| 2005/0020940 | A1 | 1/2005 | Opie et al. |
| 2006/0186010 | A1 | 8/2006 | Warnack et al. |
| 2007/0185413 | A1 | 8/2007 | Asai et al. |
| 2008/0006554 | A1 | 1/2008 | Duffy et al. |
| 2009/0264864 | A1 * | 10/2009 | Teirstein ......... A61M 25/09041 |
| | | | 604/533 |
| 2012/0078231 | A1 | 3/2012 | Hoshinouchi |
| 2012/0172846 | A1 | 7/2012 | Nakamoto et al. |
| 2013/0206623 | A1 | 8/2013 | Spaargaren et al. |
| 2014/0144798 | A1 | 5/2014 | Benesh |
| 2014/0171833 | A1 * | 6/2014 | Matsuno ................ A61B 90/57 |
| | | | 600/585 |
| 2015/0068941 | A1 | 3/2015 | Caron |
| 2016/0143616 | A1 | 5/2016 | Okubo et al. |
| 2017/0281901 | A1 | 10/2017 | Otake |

FOREIGN PATENT DOCUMENTS

| | | |
|---|---|---|
| JP | 2004290395 A | 10/2004 |
| JP | 2012055601 A | 3/2012 |
| JP | 2012070916 A | 4/2012 |
| WO | 9818515 A1 | 5/1998 |
| WO | 2011033939 A1 | 8/2011 |
| WO | 2014188509 A1 | 11/2014 |

OTHER PUBLICATIONS

International Search Report (PCT/ISA/210) dated Mar. 29, 2016, by the Japanese Patent Office as the International Searching Authority for International Application No. PCT/JP2015/083804.

Written Opinion (PCT/ISA/237) dated Mar. 29, 2016, by the Japanese Patent Office as the International Searching Authority for International Application No. PCT/JP2015/083804.

\* cited by examiner

CATHETER HOLDER AND CATHETER SET

CROSS-REFERENCES TO RELATED APPLICATIONS

This application is a continuation of U.S. patent application Ser. No. 15/609,143, filed on May 31, 2017, which is a continuation of International Application No. PCT/JP2015/083804 filed on Dec. 1, 2015, and claims the benefit of JP2014-244259 filed on Dec. 2, 2014, the entire content of each of which is incorporated herein by reference.

TECHNICAL FIELD

The present invention relates to a catheter holder and a catheter set.

DESCRIPTION

In the related art, it is known to use an image diagnosis catheter, which is referred to as an intravascular ultrasound (IVUS) diagnostic apparatus or an optical coherence tomography (OCT) diagnostic apparatus, to acquire a diagnostic image for performing diagnosis on a diseased region or the like in a living body. This type of image diagnosis catheter includes a sheath that is introduced into a living body, an outer tube that is provided at the base end side of the sheath, an inner shaft inserted into the outer tube, and a drive shaft that is rotatably driven in the sheath and moves back and forth within the sheath following the back and forth movement of the inner shaft. When the image diagnosis catheter is used, a so-called pullback operation (pulling operation) of pulling the tip end of the inner shaft from the outer tube by moving back the inner shaft and of moving the drive shaft from the tip end side to the base end side, or a push-in operation of pushing the drive shaft toward the tip end side is performed.

In general, a medical instrument having an elongated shape such as a catheter is accommodated in a container having a wound tube shape, which is called a holder tube, in order to facilitate handling and to promote protection, during transportation or in a stage before use. When the holder tube is used, an attempt is made in which a holder as described in International Publication No. WO 2011/033939 is used together to place a portion of the catheter, which is exposed from the holder tube, in a state of being held in relation to the holder tube, and to package the holder tube and the catheter in a packaging container in order to provide the holder tube and the catheter.

SUMMARY

When, for example, the holder tube is used at the time of packaging the image diagnosis catheter, an outer tube provided in the image diagnosis catheter is caused to have a bending tendency due to winding at the time of accommodation. When the above-described push-in operation is performed in a state in which the outer tube is bent, the drive shaft is likely to be kinked. Therefore, it is necessary to perform an operation of correcting the bending tendency in use, which imposes an excessive operating burden on a user. In addition, since the bending tendency may not be sufficiently eliminated even if the operation of correcting the bending tendency is performed, it is impossible to sufficiently reduce the risk of occurrence of kink of the drive shaft merely by forcing the user to perform the correcting operation.

Meanwhile, in the image diagnosis catheter, since a handle-side portion in which a hub or a connector including an electrical configuration is disposed is heavier than the other portion, a high load may be unintentionally applied to the outer tube or the inner shaft after the catheter is taken out from the packaging container and before the catheter is connected to an external device such as a motor drive unit (MDU). Therefore, when the hub or the connector is not maintained in the state in which the hub and the connector are firmly held even after the catheter is taken out from the packaging container, damage such as breakage may occur in the drive shaft.

In addition, the same problem as those described above is also found in various treatment catheters (e.g., an atherectomy catheter) used in the medical field. For example, the atherectomy catheter has the same configuration as the handle portion of the image diagnosis catheter. Thus, when the holder tube known in the related art is applied thereto, buckling or bending may occur in the handle-side base end portion of a shaft portion having a small diameter. When buckling or bending occurs, the operability of the handle portion is deteriorated, which deteriorates the insertion property of the catheter tip end portion into a body cavity such as a blood vessel, and hinders the operation of the tip end portion.

In view of the above-described problems, provided is a catheter holder, which is capable of preventing an outer tube of a catheter from being caused to have a bending tendency due to the use of a holder tube, and holding the catheter in a stable state so as to prevent an unintentional load from being applied to each part of the catheter until the use of the catheter is initiated, and a catheter set including the corresponding catheter holder. The catheter holder is used to hold a catheter in a predetermined state, and includes a sheath configured to be inserted into a body cavity of a living body, an outer tube provided on a base end side of the sheath, an inner shaft inserted into the outer tube to be movable back and forth, a connector part provided on a base end side of the outer tube and configured to accommodate the inner shaft therein, and a hub provided on a base end side of the inner shaft. The catheter holder includes: an attachment section configured to be attachable to a holder tube that accommodates at least a portion of the sheath in a wound state; a support section formed to extend from the attachment section toward a direction away from the wound holder tube; and a fixing section provided on a second end side of the support section, which is opposite to a first end side of the support section on which the attachment section is provided, the fixing section being configured to fix the connector part and/or the hub to hold the outer tube, which is exposed from an opening portion of the holder tube, in a linear shape to be fixed in position.

In addition, there is provided a catheter set including: catheter including a sheath configured to be inserted into a body cavity of a living body, an outer tube provided on a base end side of the sheath, a connector part provided on a base end side of the outer tube and configured to accommodate the inner shaft therein, and a hub provided on a base end side of the inner shaft; a holder tube configured to accommodate at least a portion of the sheath in a wound state therein; a catheter holder including an attachment section configured to be attachable to a holder tube, a support section formed to extend from the attachment section toward a direction away from the wound holder tube, and a fixing section provided on a second end side of the support section, which is opposite to a first end side of the support section on which the attachment section is provided, the fixing section being configured to fix the connector part and/or the hub to hold the outer tube, which is exposed from an opening portion of the holder tube, in a linear shape to be fixed in position; and a packaging container configured to accommodate the catheter, the holder tube, and the catheter holder therein in a state where the sheath is accommodated in the holder tube and the outer tube is held by the catheter holder.

According to the catheter holder or the catheter set configured as described above, since it is possible to prevent the outer tube from being caused to have a bending tendency due to the use of the holder tube, for example, it is possible to prevent the drive shaft from being kinked at the time of using the image diagnosis catheter. In addition, since the connector unit or the hub may be stably held while being supported relative to the holder tube until the use of the image diagnosis catheter is initiated, it is possible to prevent load from being unintentionally applied to each part of the image diagnosis catheter after the catheter is taken out the packaging container, and to prevent occurrence of damage such as breakage in the drive shaft during the operation of preparing use.

When the fixing section includes a hub-side fixing part configured to fix the hub to restrict rotation of the hub and to release fixing of the hub when force is applied in a direction of relatively separating the hub therefrom, and a connector-side fixing part configured to fix the connector part with fixing force smaller than fixing force of the hub-side fixing part for fixing the hub and to restrict a movement of the connector part in a direction away from an axial center of the outer tube, it is possible to prevent the rotation of the hub by the hub-side fixing part, thereby preventing the rotation and displacement of the entire image diagnosis catheter due to the rotation of the hub. In addition, by relatively simply fixing the connector part by the connector-side fixing part, it is possible to prevent excessive force from being applied to the connector part when releasing the holding of the image diagnosis catheter. Therefore, it is possible to hold the image diagnosis catheter in a stable state, and to prevent the inner shaft, which is inserted into the connector part, from being kinked when the image diagnosis catheter is removed.

When the support section includes a base portion formed to extend toward the hub-side fixing part so that an extension line of an extending direction of the support section overlaps a portion of the hub-side fixing part to which the force is applied when releasing the fixing of the hub, the force applied by one of left and right hands to press the base portion acts to suppress the axial shaking of the hub-side fixing part. Therefore, when performing the operation of releasing the fixing of the hub-side fixing part with the other hand, the force can be efficiently transmitted and the fixing can be smoothly released.

When the hub-side fixing part includes a first groove portion configured to accommodate the hub therein, a first opening portion configured to allow the hub to be inserted into the first groove portion therethrough, and a pull-out prevention portion configured to prevent the hub from being pulled out from the first groove portion, and the connector-side fixing part includes a second groove portion configured to accommodate the connector part therein, and a second opening portion opened toward the same direction as the first opening portion and configured to allow the connector part to be inserted into the second groove portion therethrough, the fixing by the hub-side fixing part and the connector-side fixing part can be released by lifting the hub. Therefore, after the operation of removing the catheter from the catheter holder is performed, the hub may be held as it is in a state of being gripped by fingers. Then, after the catheter is removed, it is possible to prevent load of the hub, the connector part, or the like from being applied to each part of the image diagnosis catheter, and therefore, it is possible to prevent the inner shaft or the like, which is inserted into the connector part, from being kinked after the image diagnosis catheter is removed and until the use of the catheter is initiated.

When the catheter holder further includes a length adjustment part that makes a distance between the hub-side fixing part and the connector-side fixing part variable, it is possible to draw out the inner shaft from the outer tube by increasing the distance between the hub-side fixing part and the connector-side fixing part in a state in which the hub is fixed by the hub-side fixing part and the connector part is fixed by the connector-side fixing part. Therefore, it is possible to perform the priming of the image diagnosis catheter in a state in which the inner shaft is drawn out from the outer tube and the image diagnosis catheter is held. Thus, it is possible to provide a catheter holder that is excellent in convenience.

When the catheter holder further includes a medical instrument holding part provided on the attachment section and configured to detachably fix a medical instrument attached to the catheter and to hold the medical instrument on an inner peripheral side of the wound holder tube, it is possible to hold a medical instrument along with the catheter. Therefore, it is not necessary to use a mechanism for holding each medical instrument separately from the catheter holder, and it becomes possible to provide a medical instrument in a compactly accommodated state.

BRIEF DESCRIPTION OF THE DRAWINGS

FIGS. 2A and 2B schematically illustrate the entire configuration of an image diagnosis catheter according to the exemplary embodiment, in which FIG. 2A is a side view of the image diagnosis catheter before a pullback operation (pulling operation) is performed, and FIG. 2B is a side view of the image diagnosis catheter when the pullback operation is performed.

FIGS. 3A and 3B illustrate the configuration of respective parts of the image diagnosis catheter according to the exemplary embodiment, in which FIG. 3A is an enlarged cross-sectional view illustrating the tip end side configuration of the image diagnosis catheter, and FIG. 3B is an enlarged cross-sectional view illustrating the handle-side configuration of the image diagnosis catheter.

FIGS. 4A and 4B illustrate a catheter holder according to the exemplary embodiment, in which FIG. 4A is a plan view of the catheter holder, and FIG. 4B is a perspective view of the catheter holder.

FIGS. 6A to 6C illustrate respective parts of FIG. 5 in an enlarged scale, in which FIG. 6A is an enlarged view illustrating the vicinity of an opening portion on one end side of a tube holder, FIG. 6B is an enlarged view illustrating the vicinity of a fixing portion of the catheter holder, and FIG. 6C is an enlarged view illustrating the vicinity of an attachment section of the catheter holder.

FIGS. 7A and 7B illustrate views for explaining the action of the catheter holder, in which FIG. 7A illustrates an operation example when releasing the fixing applied by a hub-side fixing part, and FIG. 7B is a perspective view illustrating the back side of the hub-side fixing part.

FIGS. 8A and 8B illustrate views for explaining the action of the catheter holder, in which FIG. 8A illustrates an operation example when releasing the fixing applied by the hub-side fixing part, and FIG. 8B is a view illustrating a positional relationship between a support portion and the hub-side fixing part of the catheter holder.

FIGS. 9A and 9B illustrate a catheter holder according to a first modification, in which FIG. 9A illustrates a state before a length adjustment portion provided in the catheter holder is used, and FIG. 9B illustrates a state when the length adjustment portion provided in the catheter holder is used.

DETAILED DESCRIPTION

Hereinafter, exemplary embodiments will be described with reference to the accompanying drawings. In addition, the following description does not limit the technical scope or the meaning of the terms described in the claims. In addition, the dimensional ratios of the drawings are exaggerated for the convenience of description, and may differ from the actual ratios.

Figure 1:
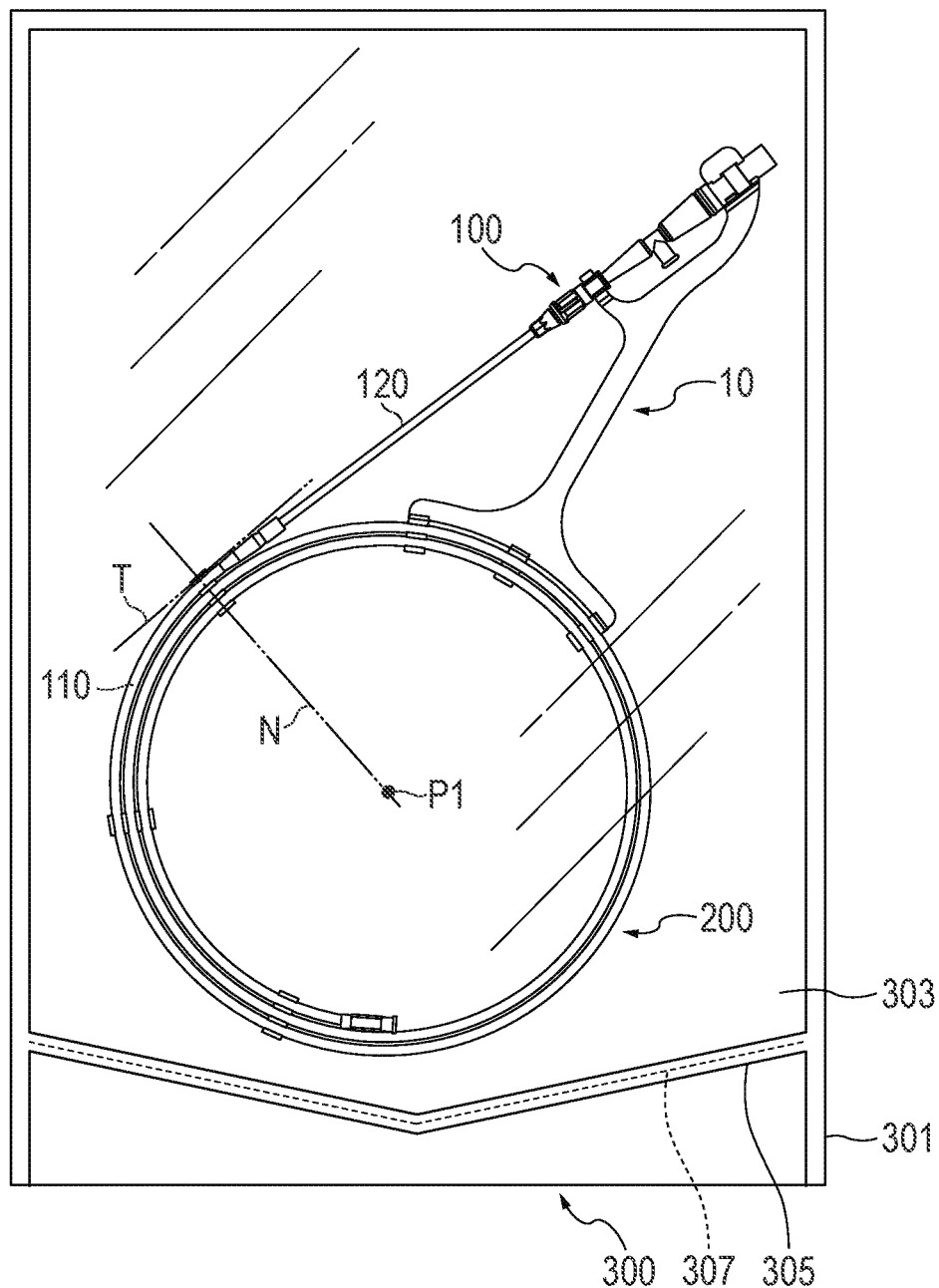
FIG. 1 is a plan view schematically illustrating a catheter set according to an exemplary embodiment.

FIG. 1 is a plan view schematically illustrating a catheter holder and a catheter set according to an exemplary embodiment, FIGS. 2A to 3B are views illustrating an image diagnosis catheter to be held by the catheter holder, and FIGS. 4A to 9B are views provided for explaining the configurations and actions of respective parts of the catheter holder.

Figure 5:
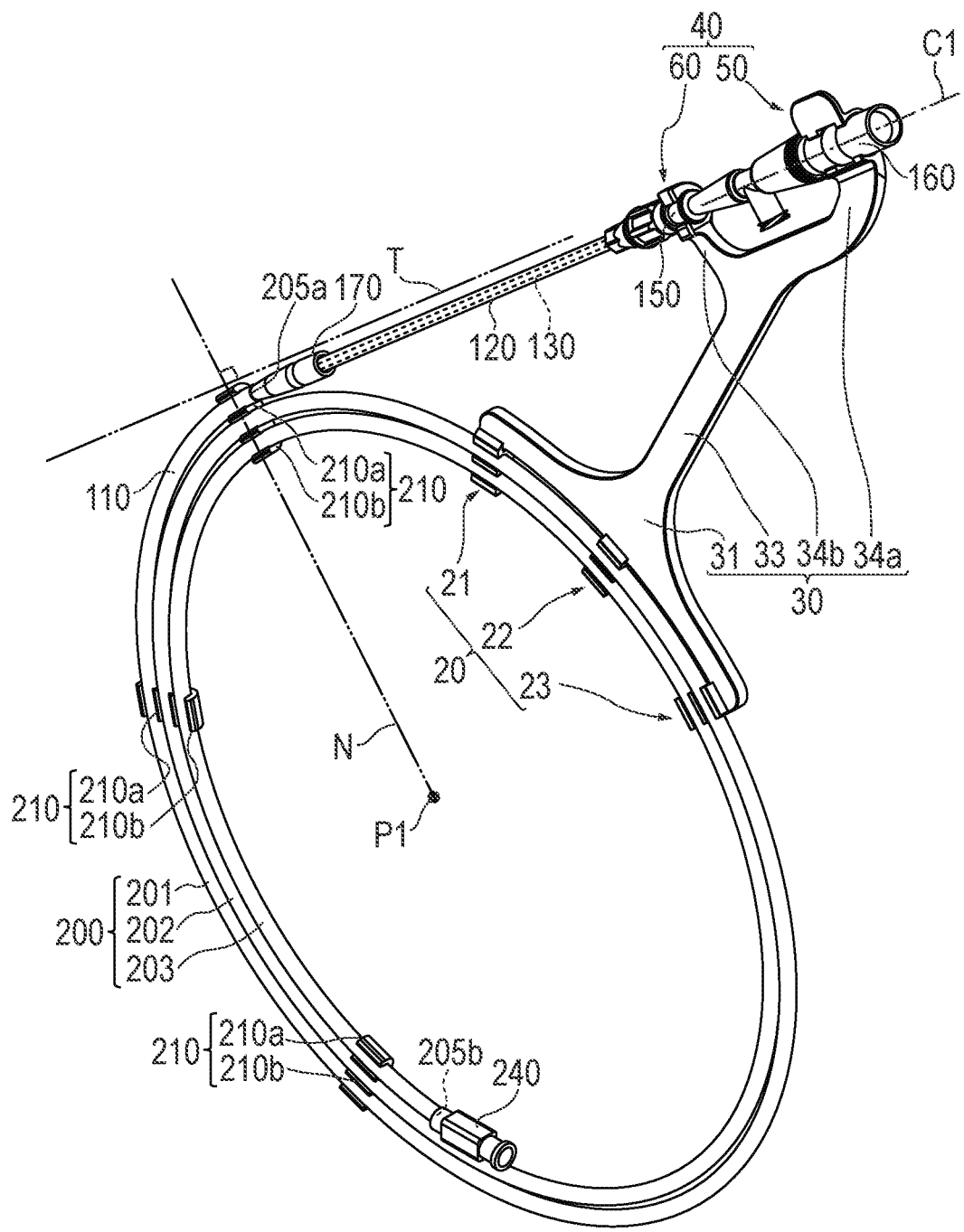
FIG. 5 is a perspective view illustrating a use state of the catheter holder according to the exemplary embodiment.

As illustrated in FIGS. 1 and 5, the catheter holder 10 according to the exemplary embodiment is configured as a holding instrument for use in holding the image diagnosis catheter 100 in a predetermined state. As will be described later, the catheter holder 10 is capable of preventing a drive shaft 140 (see FIGS. 2A and 2B) provided in the image diagnosis catheter 100 from being kinked due to a bending tendency (winding tendency) that may occur due to the use of a holder tube 200, and stably holding the image diagnosis catheter 100 until the use of the image diagnosis catheter 100 is started.

The image diagnosis catheter 100 will be described with reference to FIGS. 2A to 3B. In the description of the exemplary embodiment, an intravascular ultrasound (IVUS) diagnostic apparatus will be described as an example of the image diagnosis catheter 100.

Figure 2A:
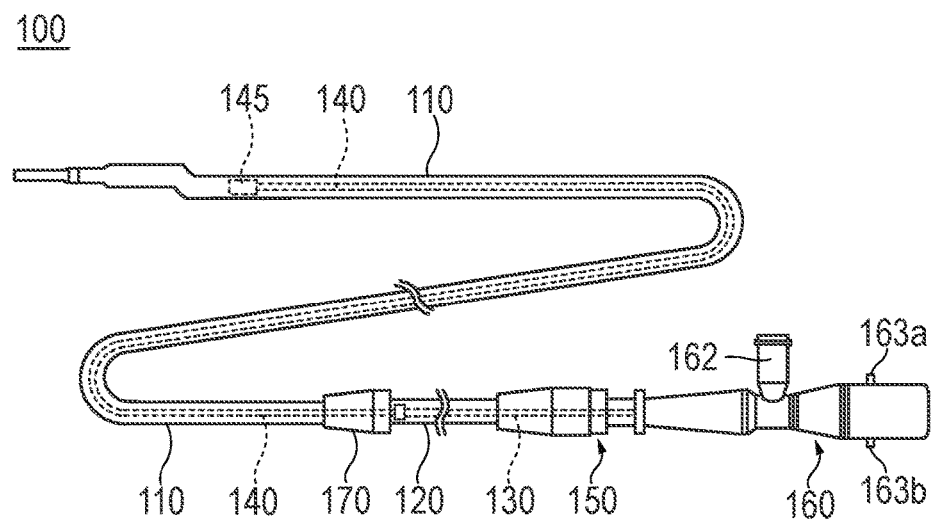
Figure 2B:
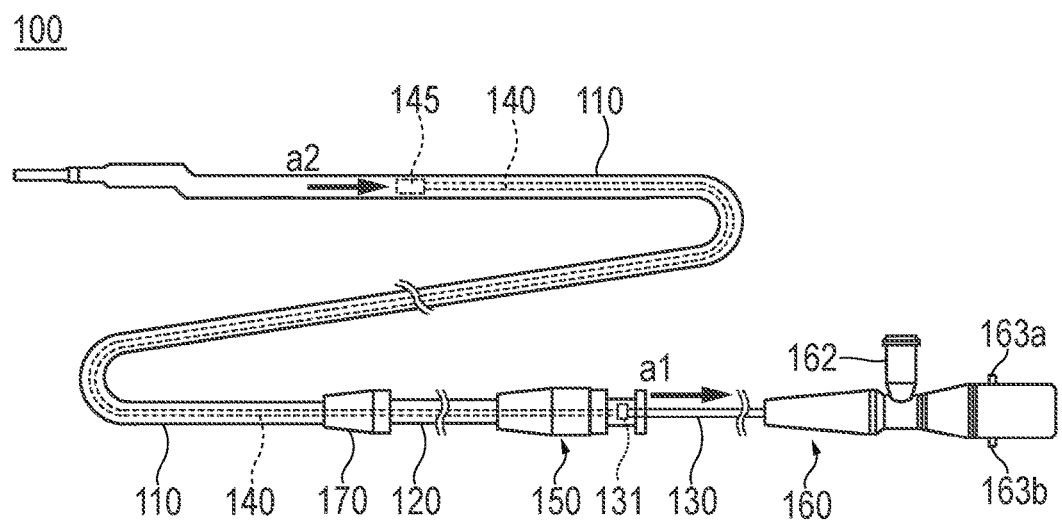

As illustrated in FIGS. 2A and 2B, roughly speaking, the image diagnosis catheter 100 includes a sheath 110 that is inserted into a body cavity of a living body, an outer tube 120 that is provided on the base end side of the sheath 110, an inner shaft 130 that is inserted into the outer tube 120 to be movable back and forth, a drive shaft 140 that is rotatably provided in the sheath 110 and has a signal transmission/reception part 145, which transmits and receives a signal, on the tip end thereof, a unit connector 150 (corresponding to a "connector part") that is provided on the base end side of the outer tube 120 and is configured to accommodate the inner shaft 130, and a hub 160 that is provided on the base end side of the inner shaft 130.

In the description of the specification, the side of the image diagnosis catheter 100 that is to be inserted into the body cavity will be referred to as the tip end or the tip end side, the side of the hub 160 provided on the image diagnosis catheter 100 will be referred to as the base end or the base end side, and the extending direction of the sheath 110 will be referred to as the axial direction.

Figure 3A:
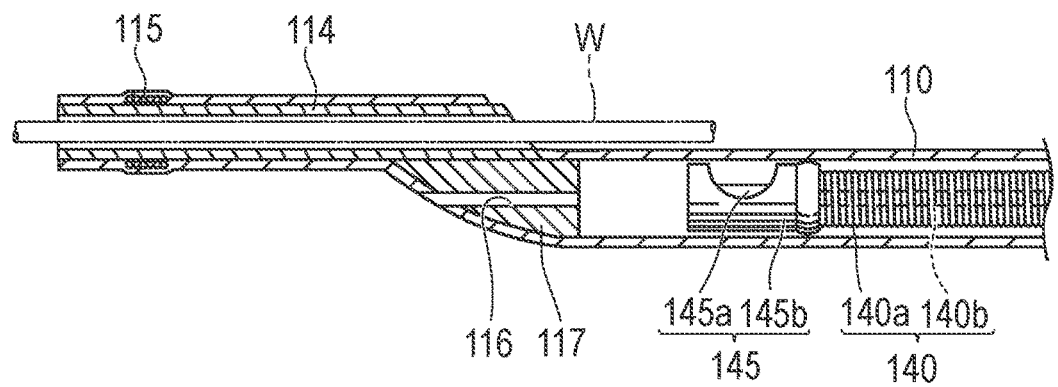
Figure 3B:
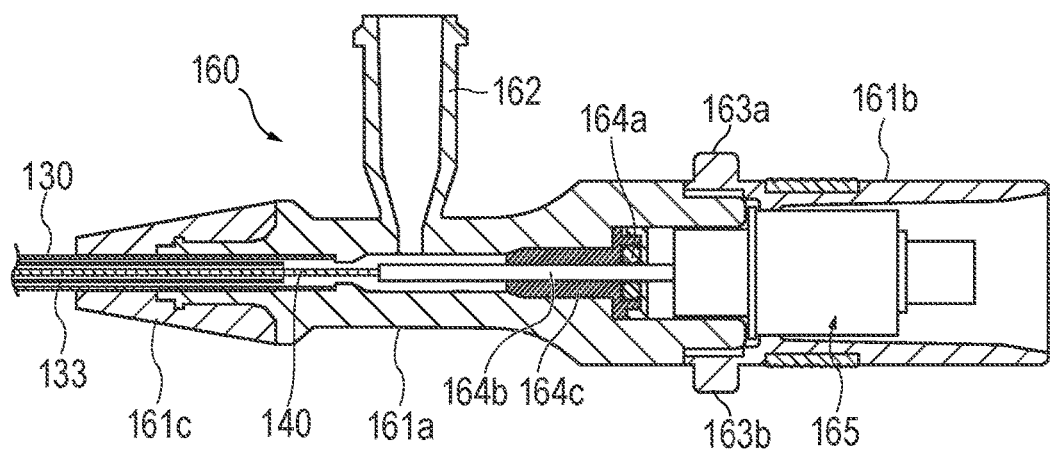

As illustrated in FIGS. 2A and 3B, the drive shaft 140 extends to the inside of the hub 160 by passing through the sheath 110, the outer tube 120 connected to the base end of the sheath 110, and the inner shaft 130 inserted into the outer tube 120.

The hub 160, the inner shaft 130, the drive shaft 140, and the signal transmission/reception part 145 are connected to each other so as to integrally move back and forth in the axial direction. Therefore, for example, when an operation of pushing the hub 160 toward the tip end side is performed, the inner shaft 130 connected to the hub 160 is pushed into the outer tube 120 and the unit connector 150, and the drive shaft 140 and the signal transmission/reception part 145 are moved to the tip end side inside the sheath 110. In addition, when an operation of pulling the hub 160 to the base end side is performed, the inner shaft 130 is drawn out from the outer tube 120 and the unit connector 150 as indicated by the arrow a1 in FIG. 2B, and the drive shaft 140 and the signal transmission/reception part 145 are moved to the base end side inside the sheath 110 as indicated by the arrow a2 in FIG. 2B.

As illustrated in FIG. 2A, when the inner shaft 130 is fully pushed to the tip end side, the tip end portion of the inner shaft 130 reaches the vicinity of a relay connector 170. At this time, the signal transmission/reception part 145 is located near the tip end of the sheath 110. The relay connector 170 is a connector that interconnects the sheath 110 and the outer tube 120.

As illustrated in FIG. 2B, a pull-out prevention connector 131 is provided on the tip end of the inner shaft 130. The pull-out prevention connector 131 functions to prevent the inner shaft 130 from being pulled out from the outer tube 120. The pull-out prevention connector 131 is configured to be caught, at a predetermined position, by the inner wall of the unit connector 150 when the hub 160 is fully pulled to the base end side, that is, when the inner shaft 130 is fully drawn out from the outer tube 120 and the unit connector 150.

As illustrated in FIG. 3A, the drive shaft 140 includes a flexible pipe body 140a and a signal line 140b inserted into the pipe body 140a. The pipe body 140a may be configured by, for example, a coil of multiple layers having different winding directions around an axis. A constituent material of the coil may be, for example, stainless steel or a Ni—Ti (nickel-titanium) alloy.

The signal transmission/reception part 145 includes an ultrasonic oscillator 145a that transmits and receives ultrasonic waves and a housing 145b in which the ultrasonic oscillator 145a is accommodated. The ultrasonic oscillator 145a is electrically connected to the signal line 140b. The signal line 140b may be configured by, for example, a twisted pair cable or a coaxial cable. The ultrasonic oscillator 145a functions to transmit ultrasonic waves as examination waves into the body cavity and to receive the ultrasonic waves reflected from the body cavity.

On the tip end portion of the sheath 110, a priming liquid discharge member 117 having a priming liquid discharge hole 116 is provided to discharge priming liquid. When the image diagnosis catheter 100 is used, the sheath 110 is filled with the priming liquid in order to reduce the attenuation of ultrasonic waves by air in the sheath 110 and to ensure efficient transmission/reception of ultrasonic waves. Through the filling of the priming liquid, gas such as the air staying in the sheath 110 may be discharged from the priming liquid discharge hole 116 that is formed in the priming liquid discharge member 117.

A guide wire insertion member 114 having a lumen, into which a guide wire W may be inserted, is attached to the tip end of the sheath 110. In addition, a marker 115 having an X-ray contrast property is provided on the guide wire insertion member 114.

As illustrated in FIG. 3B, the hub 160 includes a hub body 161a having a hollow shape, a joint 161b in which a connector 165 is disposed to be mechanically and electrically connected to a motor drive unit (not illustrated), an anti-kink protector 161c, a port 162 that communicates with the inside of the hub body 161a, direction confirmation protrusions 163a and 163b for confirming the direction of the hub 160 when performing connection with the motor drive unit, a seal member 164a that seals the base end side relative to the port 162, a connection pipe 164b that holds the drive shaft 140, and a bearing 164c that rotatably supports the connection pipe 164b.

The inner shaft 130 is connected to the tip end of the hub body 161a. The drive shaft 140 is drawn out from the inner shaft 130 in the inside of the hub body 161a. A protective tube 133 is disposed between the inner shaft 130 and the drive shaft 140. The protective tube 133 functions to prevent damage to the drive shaft 140 due to interference between the inner shaft 130 and the drive shaft 140.

The drive shaft 140 is connected to the tip end of the connection pipe 164b. The connector 165 is connected to the base end of the connection pipe 164b. The connection pipe 164b and the drive shaft 140 are rotated in conjunction with the rotation of the connector 165. The signal line 140b (see FIG. 3A) disposed inside the drive shaft 140 is inserted into the inside of the connection pipe 164b and electrically connected to the connector 165.

When the image diagnosis catheter 100 configured as described above is used, first, the hub 160 is connected to the motor drive unit. Then, a pullback operation is performed to move back the drive shaft 140 and the signal transmission/reception part 145 toward the base end side of the sheath 110 from a state in which the drive shaft 140 and the signal transmission/reception part 145 are disposed on the tip end side of the sheath 110. At this time, the drive shaft 140 and the signal transmission/reception part 145 are rotated (radially scanned) by drive force provided by the motor drive unit. When the signal transmission/reception part 145 is moved in the axial direction by performing the pullback operation, it becomes possible to acquire a 360 degree tomographic image of a surrounding organic body in the axial direction inside a living body lumen (e.g., a blood vessel).

Next, the catheter holder 10 and the catheter set 1 will be described.

Referring to FIGS. 1 and 5, the catheter holder 10 may be accommodated (packaged), together with the holder tube 200, in the packaging container 300 in the state of holding the image diagnosis catheter 100. The catheter set 1 is constituted by the catheter holder 10, the image diagnosis catheter 100, the holder tube 200, and the packaging container 300 in which these respective members are accommodated.

As the packaging container 300, for example, a peel bag, which is generally used for packaging medical instruments, may be used. The packaging container 300 illustrated in FIG. 1 includes a mounting sheet 301 that constitutes a base material of the packaging container 300, and a film portion 303 attached onto the mounting sheet 301 to define a bag-shaped portion having a predetermined volume (shape). In addition, in order to keep the inside of the packaging container 300 in a sterilized state, the packaging container 300 includes an opening portion 305 formed on the upper side of the film portion 303 and a sealing portion 307 that seals the opening portion 305.

The packaging container 300 is configured in a vertically elongated bag shape having a volume that is capable of accommodating the catheter holder 10, the image diagnosis catheter 100, and the holder tube 200. The film portion 303 of the packaging container 300 may be formed, for example, to be transparent or translucent in order to secure internal visibility. In addition, in order to enable ethylene oxide gas (EOG) sterilization to be performed on the catheter holder 10, the image diagnosis catheter 100, and the holder tube 200 in a state in which these members are accommodated in the packaging container 300, for example, the mounting sheet 301 disposed on the back side of the packaging container 300 may be formed of a gas-permeable nonwoven fabric or the like.

By accommodating the sheath 110 of the image diagnosis catheter 100, the holder tube 200 accommodates the sheath 110 of the image diagnosis catheter 100, thereby prevents the sheath 110 from being fixed in an unstable state when the sheath 10 is handled in a linear shape, prevents the dimension of the major axis of the sheath 110 (the axial length of the sheath 110) from being increased, and prevents the sheath 110 from being damaged due to friction with a peripheral device during transportation or the like. The holder tube 200 is configured by a hollow elongated member having sufficient flexibility to be manually wound. A constituent material of the holder tube 200 may be, for example, a resin material such as polyethylene or polypropylene.

As illustrated in FIG. 5, an opening portion 205a is formed on one end side of the holder tube 200 and an opening portion 205b is formed on the other end side of the holder tube 200. The sheath 110 may be accommodated in the holder tube 200 by inserting the tip end side of the sheath 110 into the inside of the holder tube 200 through the opening portion 205a on the one end side of the holder tube 200, and performing a push-in operation of the sheath 110.

A connector port 240 is provided in the opening portion 205b formed on the other end side of the holder tube 200 to be connectable to a syringe for supplying priming liquid, or the like. The connector port 240 is connected to the syringe when a priming processing is performed on the holder tube 200.

As illustrated in FIG. 5, the holder tube 200 is wound around a winding center P1 a predetermined number of times, so as to form a substantially circular outer shape. In the exemplary embodiment, the holder tube 200 is wound around the winding center P1 by about two and half turns from the opening portion 205a on one end side to the opening portion 205b on the other end side, thereby forming the holder tube 200 into the circular outer shape. In addition, the number of times of winding the holder tube 200, the external dimensions of the holder tube 200, and the like after wound are not particularly limited.

In the holder tube 200, for convenience, respective wound portions are referred to as a first wound portion 201, a second wound portion 202, and a third wound portion 203. The first wound portion 201 is the portion that is located on the outermost periphery of the holder tube 200, the third wound portion 203 is the portion that is located on the innermost periphery of the holder tube 200, and the second wound portion 202 is the portion that is located in an intermediate portion between the innermost periphery and the outermost periphery of the holder tube 200.

In order to keep the holder tube 200 in the wound state, multiple fixing members 210 may be used, for example, as illustrated in FIG. 5. Each fixing member 210 is formed with a groove portion, into which the holder tube 200 may be fitted to be fixed in position.

Each fixing member 210 includes a first fixing portion 210a in which a groove portion is formed to fix the first wound portion 201 of the holder tube 200 and a second fixing portion 210b in which a groove portion is formed to fix the third wound portion 203 of the holder tube 200. Each fixing member 210 is configured to fix the holder tube 200 at two positions. By inserting the holder tube 200 into the groove portions of each fixing member 210, it is possible to simply fix the holder tube 200, to prevent the respective wound portions 201, 202 and 203 of the holder tube 200 from being displaced, or to prevent the outer shape of the holder tube 200 from being enlarged. In addition, although the number of fixing members 210 to be used is not limited, for example, as illustrated in FIG. 5, three fixing members 210 may be used to fix the wound holder tube 200 at different positions in the peripheral direction thereof.

As illustrated in FIG. 5, the holder tube 200 may be configured to have a length that is capable of covering the entire sheath 110 of the image diagnosis catheter 100 and an inner diameter that is capable of accommodating the sheath 110. In addition, the specific dimensions (e.g., length, inner diameter, and outer diameter) of each part of the holder tube 200 may be appropriately changed according to the dimensions of the sheath 110 of the image diagnosis catheter 100 to be accommodated, and are not particularly limited.

In the image diagnosis catheter 100, respective parts located closer to the base end side than the sheath 110 are exposed from the holder tube 200. Specifically, as illustrated in FIG. 5, the relay connector 170 disposed near the opening portion 205a on one end side of the holder tube 200, the outer tube 120 into which the inner shaft 130 is inserted, the unit connector 150, and the hub 160 are exposed from the holder tube 200. The parts exposed from the holder tube 200 are held by the catheter holder 10 until the image diagnosis catheter 100 is used (e.g., from the time of product shipment to the time of being connected to a motor drive unit when in use).

Figure 4A:
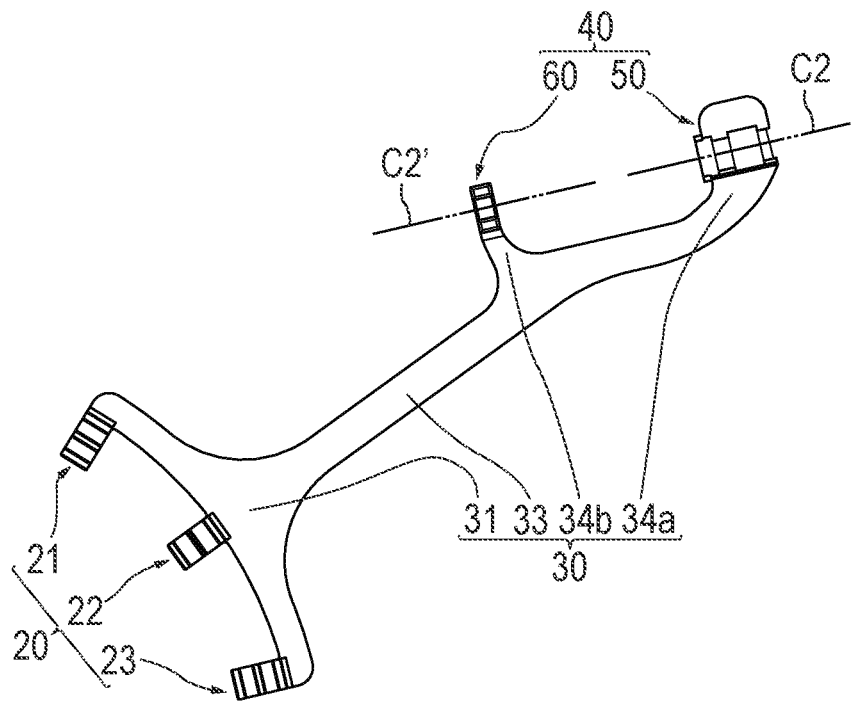
Figure 4B:
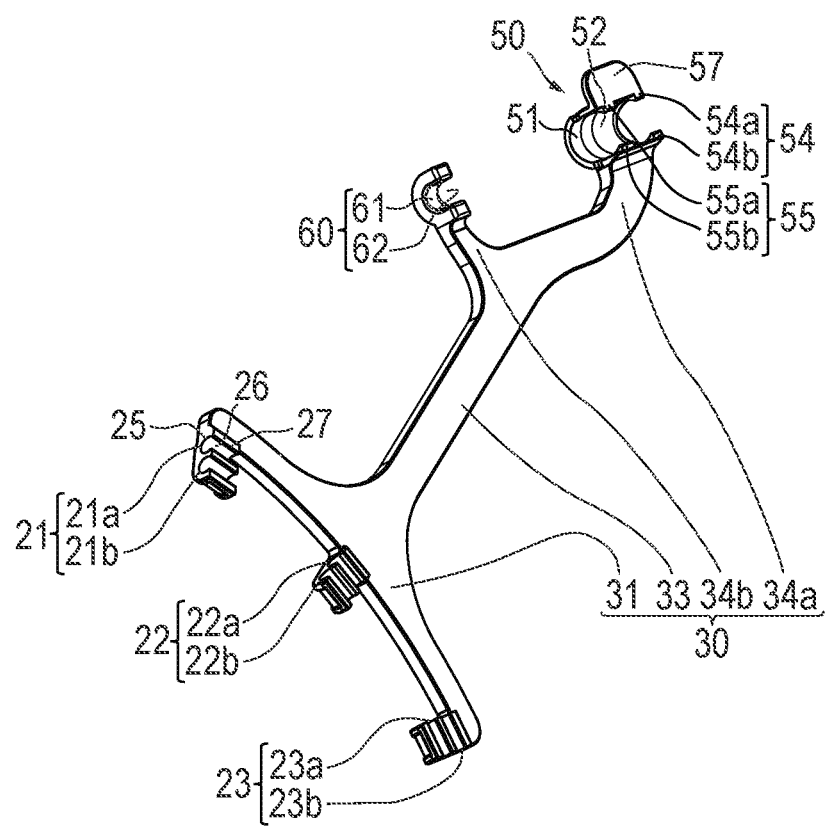

As illustrated in FIGS. 4A, 4B, and 5, the catheter holder 10 includes an attachment section 20 that is attachable to the holder tube 200, a support section 30 that extends from the attachment section 20 toward a direction away from the wound holder tube 200, and a fixing section 40 that is provided on a second end side of the support section 30 that is opposite to a first end side on which the attachment section 20 is provided. In addition, the terms "first end side" and "second end side" indicate a relative positional relationship between the attachment section 20, the support section 30, and the fixing section 40, and do not mean specific ends of the catheter holder 10.

Each of the attachment section 20, the support section 30, and the fixing section 40, which constitute the catheter holder 10, may be integrally formed through injection molding or the like. Although a constituent material is not particularly limited, in the present embodiment, each section is formed of ABS resin. As other constituent materials, for example, a hard resin material such as, polyethylene terephthalate, polymethyl methacrylate, or polycarbonate, glass, or ceramics, may be used. In addition, each member or any member of the attachment section 20, the support section 30, and the fixing section 40 may be formed as a separate body and configured to be separable from and connectable to each other.

As illustrated in FIGS. 4B and 5, the attachment section 20 of the catheter holder 10 includes a first connecting part 21, a second connecting part 22, and a third connecting part 23, each of which is detachably attached to the holder tube 200.

The respective connecting parts 21, 22, and 23 are provided at a predetermined interval in the extending direction (width direction) of an arm portion 31 provided in the support section 30. When the holder tube 200 and the catheter holder 10 are connected to and integrated with each other by disposing the multiple connecting parts 21, 22 and 23 on the attachment section 20, it is possible to prevent (reduce) unintentional rotation of the holder tube 200 and the catheter holder 10 in the winding direction (radial direction) of the holder tube 200.

The first connecting part 21 includes a first fixing portion 21a connected to the second wound portion 202 of the holder tube 200 and a second fixing portion 21b connected to the third wound portion 203 of the holder tube 200. The first fixing portion 21a and the second fixing portion 21b are disposed to be adjacent to each other along the radial direction of the wound holder tube 200.

As illustrated in FIG. 4B, the first fixing portion 21a provided in the first connecting part 21 includes a groove portion 25 in which the holder tube 200 is accommodated, and an opening portion 26 that allows the holder tube 200 to be inserted into the groove portion 25 therethrough.

The groove portion 25 of the first fixing portion 21a is formed to have a snap shape in cross section, which has a width that is substantially equal to or smaller than the outer diameter of the holder tube 200. That is, the first fixing portion 21a has a snap-fit structure to mechanically fix the holder tube 200 by causing the holder tube 200 to be fitted into the groove portion 25. When the holder tube 200 is inserted into the groove portion 25 through the opening portion 26 of the first fixing portion 21a, the inner surface of the groove portion 25 is abutted on the outer surface of the holder tube 200. With this abutment, frictional force is applied between the holder tube 200 and the groove portion 25, causing the holder tube 200 to be fixed. In addition, in order to prevent the separation of the holder tube 200, a pull-out prevention portion 27 is provided in the vicinity of the opening portion 26 of the first fixing portion 21a to partially extend to the upper side of the groove portion 25, thereby increasing the fixing force of the holder tube 200.

The second fixing portion 21b provided in the first connecting part 21 has the same configuration as the first fixing portion 21a provided in the first connecting part 21, and thus, a detailed description of the second fixing portion 21b will be omitted. The configuration of a first fixing portion 22a and a second fixing portion 22b provided in the second connecting part 22 differs from that of the first connecting part 21. Groove portions provided in the first fixing portion 22a and the second fixing portion 22b are formed into a U-shaped cross section, and no pull-out prevention portion is provided in the vicinity of an opening portion. In addition, the configuration of the first fixing portion 22a and the second fixing portion 22b provided in the second connecting part 22 may be the same as that of the first connecting part 21 in order to increase the fixing force for the holder tube 200. In addition, a first fixing portion 23a and a second fixing portion 23b provided in the third connecting part 23 have the same configuration as the first fixing portion 21a provided in the first connecting part 21. Thus, detailed descriptions of the first and second fixing portions of the second and third connecting parts will be omitted.

So long as the attachment section 20 is detachably attached to the holder tube 200, attachment positions with respect to the holder tube 200, the number of attachment locations (the number of connecting parts and the number of fixing portions), and the like are not particularly limited. However, as in the exemplary embodiment, when the attachment section 20 is configured such that the multiple connecting parts 21, 22 and 23 provided in the attachment section 20 are attached to the different wound portions 202 and 203 of the holder tube 200 at different positions in the peripheral direction of the wound holder tube 200, the fixing force for the holder tube 200 may be increased. In addition, when each of the connecting parts 21, 22 and 23 of the attachment section 20 is provided with the multiple fixing portions, which are adjacent to each other in the radial direction of the holder tube 200, it is possible to prevent the outer shape of the holder tube 200 from being unintentionally enlarged due to the displacement of the respective wound portions 201, 202 and 203 of the holder tube 200.

As illustrated in FIGS. 4A and 5, the support section 30 of the catheter holder 10 includes the arm portion 31 on which the attachment section 20 is provided, a base portion 33 that extends from the arm portion 31 to the fixing section 40, which is fixed to the imaging diagnosis catheter 100, and a first branch portion 34a and a second branch portion 34b, which are bifurcated from the base portion 33.

The support section 30 is disposed so as to generally extend away from the holder tube 200 (toward the other end side) while being attached to the holder tube 200. The support section 30 extends between one end side provided with the attachment section 20 and the other end side provided with the fixing section 40, and configures an intermediate portion (connecting portion) of the attachment section 20 and the fixing section 40.

The arm portion 31 provided in the support section 30 has a curved outer shape having substantially the same curvature as the outer contour line of the wound holder tube 200. As described above, the connecting parts 21, 22, and 23, which constitute the attachment section 20, are provided on the arm portion 31 of the support section 30. Since the arm portion 31 is curved at substantially the same curvature as the outer contour line of the wound holder tube 200, the respective connecting parts 21, 22 and 23 may be disposed along the outer contour line of the wound holder tube 200. Thereby, the respective connecting parts 21, 22 and 23 may be fixed to the holder tube 200 without damaging the outer shape of the wound holder tube 200.

The base portion 33 provided in the support section 30 is shaped so as to substantially linearly extend in a predetermined direction in consideration of operability when releasing the fixing of the image diagnosis catheter 100 by the fixing section 40. The action of the base portion 33 will be described later.

The first branch portion 34a provided in the support section 30 extends toward a hub-side fixing part 50 provided in the fixing section 40. In addition, the second branch portion 34b provided in the support section 30 extends toward a connector-side fixing part 60 provided in the fixing section 40. As illustrated in FIG. 7B, a concave groove portion 36 is formed on the back surface of the first branch portion 34a. The groove portion 36 may be used as a finger hooking portion to be hooked by a finger when releasing fixing by the fixing section 40.

Figure 6A:
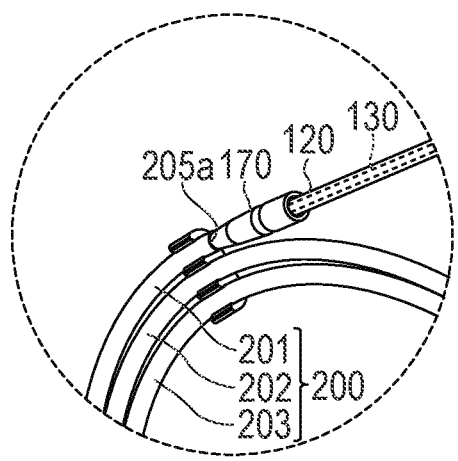
Figure 6B:
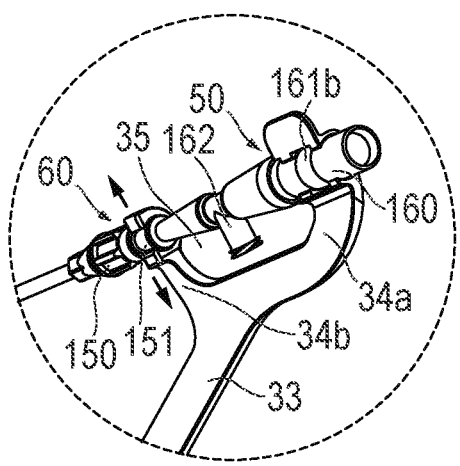
Figure 6C:
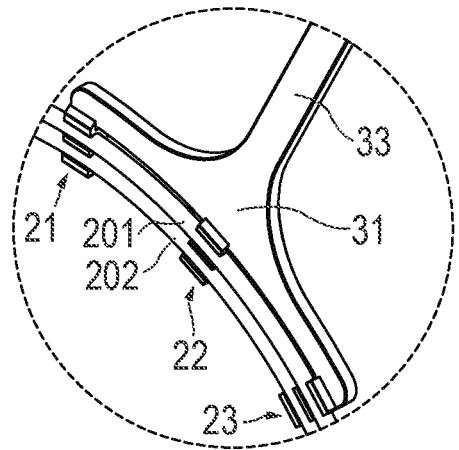

As illustrated in FIG. 6B, a predetermined concave portion 35 is provided between the first branch portion 34a and the second branch portion 34b. The port 162 of the image diagnosis catheter 100, which is held by the catheter holder 10, may be accommodated in the concave portion 35. When the port 162 is accommodated in the concave portion 35, it is possible to prevent the port 162 from protruding to the outside of the catheter holder 10, which enables the image diagnosis catheter 100 to be held in a more compact state. In addition, when the catheter holder 10 is oriented such that the port 162 is disposed in the concave portion 35, it is possible to define the direction of the image diagnosis catheter 100 whenever the catheter holder 10 is used, which may improve the ease of use of the catheter holder 10.

As illustrated in FIGS. 4B and 5, the fixing section 40 provided in the catheter holder 10 includes the hub-side fixing part 50 that fixes the hub 160 of the image diagnosis catheter 100, and the connector-side fixing part 60 that fixes the unit connector 150 of the image diagnosis catheter 100.

The hub-side fixing part 50 fixes the hub 160 of the image diagnosis catheter 100 with relatively large fixing force, and also prevents rotation, so that the image diagnosis catheter 100 can be held in a stable state.

A handle-side constituent member, including the hub 160 or the like of the image diagnosis catheter 100, generally has a substantially circular cross-sectional shape centering on an axis C1 that extends along the extending direction of the image diagnosis catheter 100. In addition, when the handle-side constituent member including the hub 160 or the like, is fixed, the hub 160 may be weak against the force acting in the direction perpendicular to a fixed surface thereof, and the hub 160 may be relatively easily released from the fixed state. Thus, unless sufficient fixing force is applied to the hub 160 or the like when holding the image diagnosis catheter 100, the hub 160 is released from the fixed state by the force applied in the direction perpendicular to the fixed surface of the hub 160. In addition, when a mechanism for sufficiently preventing the rotation is not provided, the entire image diagnosis catheter 100 may be unintentionally rotated around the axis C1, which makes it difficult to perform holding in a stable state. Therefore, the hub-side fixing part 50 may function to apply sufficient fixing force to securely fix the entire image diagnosis catheter 100 to the hub 160 and to prevent the rotation of the image diagnosis catheter 100, so as to hold the image diagnosis catheter 100 in a stable state. In addition, since the hub 160 is generally formed of a hard resin material or the like so as not to be easily deformed by external force, when performing fixing by the hub-side fixing part 50 or releasing the fixing, no deformation of the hub 160 may be caused and unintentional force may be prevented from being applied to various constituent members accommodated in the hub 160.

The connector-side fixing part 60 fixes the unit connector 150 with fixing force that is smaller than the fixing force by which the hub-side fixing part 50 fixes the hub 160, thereby restricting the movement of the unit connector 150 in the direction separating from the axial center of the outer tube 120 (the direction of the arrow in FIG. 6B).

When the catheter holder 10 is used, fixing force may be applied to the entire image diagnosis catheter 100 by fixing the hub 160 using the hub-side fixing part 50 as described above. Therefore, even when the fixing force applied to any region excluding the hub 160 is set to be relatively small, the function of stably holding the image diagnosis catheter 100 is not impaired. In addition, since the inner shaft 130 is accommodated inside the unit connector 150 (see FIG. 2B), the inner shaft 130 inside the unit connector 150 may be kinked when relatively large force is applied while fixing is performed by the connector-side fixing part 60 or the fixing is released. However, the occurrence of kink may be prevented by setting the fixing force to be applied by the connector-side fixing part 60 to a small value. In addition, when the unit connector 150, which is heavier than the outer tube 120, the inner shaft 130, or the like, is fixed and movement of the unit connector 150 in the direction away from the axial center is restricted, the occurrence of displacement in the entire image diagnosis catheter 100 starting from the displacement of the unit connector 150 may be appropriately prevented.

As described above, when the hub 160 is securely fixed by the hub-side fixing part 50 provided in the fixing section 40, and thereafter, the unit connector 150 is fixed in an auxiliary manner by the connector-side fixing part 60 provided in the fixing section 40, the held state (fixed state) of the image diagnosis catheter 100 may be stably maintained.

As illustrated in FIG. 4B, the hub-side fixing part 50 includes a first groove portion 51 that is capable of accommodating the hub 160, a first opening portion 52 that allows the hub 160 to be inserted into the first groove portion 51 therethrough, and a first pull-out prevention portion 54 and a second pull-out prevention portion 55, which prevent the hub 160 from being pulled out from the first groove portion 51.

The first groove portion 51 of the hub-side fixing part 50 has a U-shaped cross section that enables the hub 160 to be accommodated therein. The first opening portion 52 is opened to the upper side of the first groove portion 51 so as to face the outside of the first groove portion 51. In the same manner as the first fixing portion 21a, the hub-side fixing part 50 has a snap-fit structure to mechanically fix the hub 160 by inserting the hub 160 into the first groove portion 51.

Although the outer shape dimension of the hub-side fixing part 50 may be appropriately changed according to the dimension of the hub 160 so as to fix the hub 160, for example, as illustrated in FIG. 5, the hub-side fixing part 50 may be sized to expose the base end of the hub 160 from the first groove portion 51 by a predetermined length in a state in which the hub 160 is disposed in the first groove portion 51. When the hub-side fixing part 50 is configured to have this size, as will be described later, the hub 160 may be directly lifted with a finger (see FIG. 7A) when releasing the fixing of the hub 160, which may improve workability when releasing the fixing.

The pull-out prevention portions 54 and 55 are formed on the finger hooking portion 57 and the end of the first branch portion 34a, which are disposed adjacent to the first opening portion 52. Specifically, the first pull-out prevention portion 54 is configured by a protruding piece 54a, which protrudes from the finger hooking portion 57 toward the first opening portion 52, and a protruding piece 54b, which protrudes from the end of the first branch portion 34a of the support section 30 toward the first opening portion 52. In addition, the second pull-out prevention portion 55 includes a protruding piece 55a, which protrudes from the finger hooking portion 57 toward the first opening portion 52, and a protruding piece 55b, which protrudes from the end of the first branch portion 34a of the support section 30 toward the first opening portion 52.

The respective protruding pieces 54a and 54b of the first pull-out prevention portion 54 are disposed to face each other, and apply fixing force to the hub 160 so as to push the upper surface side of the hub 160 when the hub 160 is inserted into the first groove portion 51. In addition, a gap, which has a smaller length than the outer diameter of the hub 160, is provided between the protruding pieces 54a and 54b. Therefore, when the hub 160 is inserted into the first groove portion 51, an operation of pushing the hub 160 is performed after widening the gap between the protruding pieces 54a and 54b. When inserting the hub 160 into the first groove portion 51, it is necessary to apply a certain degree of push force to the hub 160 using fingers or the like. When taking the hub 160 out from the first groove portion 51, it is necessary to apply force that is required for lifting the hub 160.

The second pull-out prevention portion 55 has the same function as the first pull-out prevention portion 54, and prevents the separation of the hub 160 inserted into the first groove portion 51 by the respective protruding pieces 55a and 55b. The second pull-out prevention portion 55 is disposed at a predetermined interval in the axial direction from the first pull-out prevention portion 54. When the hub 160 is fixed at two different positions in the axial direction by the first pull-out prevention portion 54 and the second pull-out prevention portion 55, the force applied in the direction perpendicular to the fixed surface of the hub 160 may be suppressed, which may increase the fixing force for the hub 160.

In addition, the number of provided pull-out prevention portions 54 and 55 is not particularly limited, and three or more pull-out prevention portions may be provided, or only one pull-out prevention portion may be provided. However, when one pull-out prevention portion is installed, in order to increase the fixing force of the hub-side fixing part 50, the pull-out prevention portion may be configured to apply fixing force to the hub 160 within a certain length (section) along the axial direction.

As illustrated in FIG. 7B, a groove portion 58 having a notch shape is formed on the back surface of the hub-side fixing part 50 to accommodate the direction confirmation protrusions 163a and 163b provided in the hub 160 therein. When the protrusion 163a is accommodated in the notch-shaped groove portion 58, it is possible to prevent the protrusion 163a from excessively protruding to the outside. Thereby, when the image diagnosis catheter 100 is accommodated in the packaging container 300 (see FIG. 1), it is possible to prevent the film portion 303 from being damaged due to interference between the protrusion 163a and the film portion 303 of the packaging container 300. In addition, although a notch-shaped groove portion for accommodating the direction confirmation protrusion 163b is not illustrated, it is formed on the back surface of the hub-side fixing part 50 so as to form a pair with the groove portion 58 illustrated in FIG. 7B.

As illustrated in FIG. 6B, the portion of the hub 160 fixed by the hub-side fixing part 50 may be set to the joint 161b (see FIG. 3B) that is located on the base end of the hub 160. Since the joint 161b of the hub 160 is the portion that is mechanically connected to the motor drive unit, generally, no additional structure may be provided on the joint 161b and the joint 161b may have a smooth outer shape in many cases. In addition, even in different types of image diagnosis catheters, the shape of the joint 161b may be common in many cases. Therefore, when the catheter holder 10 is configured to fix the joint 161b, multiple different image diagnosis catheters may share the catheter holder 10. However, the portion to be fixed by the hub-side fixing part 50 is not limited to the joint 161b, but may be any one portion of the hub 160.

The finger hooking portion 57 formed on the hub-side fixing part 50 is configured to allow an operator to hook a finger with the finger hooking portion 57 when releasing the fixing of the hub 160 by the hub-side fixing part 50 (see FIG.

7A). The finger hooking portion 57 is formed in a wide flat plate shape to protrude outward from the hub-side fixing part 50.

As illustrated in FIG. 4B, the connector-side fixing part 60 includes a second groove portion 61 that accommodates the unit connector 150, and a second opening portion 62 that allows the unit connector 150 to be inserted into the second groove portion 61 therethrough. The second opening portion 62 of the connector-side fixing part 60 is opened toward the same direction as the first opening portion 52 of the hub-side fixing part 50 (the direction perpendicular to the paper surface of FIG. 4A).

As described above, the connector-side fixing part 60 is the part that fixes the unit connector 150 with relatively low fixing force. Therefore, the connector-side fixing part 60 is not provided with the pull-out prevention portions 54 and 55 provided in the hub-side fixing part 50. When the unit connector 150 is fixed by the connector-side fixing part 60, the unit connector 150 is inserted into the second groove portion 61 through the second opening portion 62. The wall portion around the second groove portion 61 is abutted on the outer surface of the unit connector 150, thereby applying sufficient fixing force to prevent the displacement of the unit connector 150. In addition, the fixing by the connector-side fixing part 60 may be released by simply lifting the unit connector 150 from the second groove portion 61 with relatively small force, and it is not necessary to apply large force required when releasing the fixing by the hub-side fixing part 50.

As illustrated in FIG. 6B, the portion of the unit connector 150 to be fixed by the connector-side fixing part 60 may be set to, for example, a cylindrical smooth portion 151 located on the base end of the unit connector 150. However, the portion to be fixed by the connector-side fixing part 60 is not limited to this portion, but may be any one portion of the unit connector 150.

As illustrated in FIG. 4A, the hub-side fixing part 50 and the connector-side fixing part 60 are formed such that the center axes C2 and C2' passing through respective center positions thereof linearly overlap each other. As illustrated in FIG. 5, when the image diagnosis catheter 100 is held using the catheter holder 10, the center axis C2 of the hub-side fixing part 50 and the center axis C2' of the connector-side fixing part 60 are disposed to overlap the axis C1 that extends along the extending direction of the image diagnosis catheter 100. With this arrangement, the extending direction of the first groove portion 51 of the hub-side fixing part 50 and the extending direction of the second groove portion 61 of the connector-side fixing part 60 are aligned so as to substantially linearly overlap the extending direction of the image diagnosis catheter 100. When the hub 160 is fixed to the hub-side fixing part 50 and the unit connector 150 is fixed to the connector-side fixing part 60 in such an arrangement state, the hub 160 and the unit connector 150 are disposed on the axis C1 that extends along the extending direction of the image diagnosis catheter 100. In addition, when the direction of the opening portion 205a formed on one end side of the holder tube 200 is adjusted such that the outer tube 120, exposed from the holder tube 200, is disposed on the axis C1 that extends along the extending direction of the image diagnosis catheter 100 (see FIG. 5), the outer tube 120, the unit connector 150, and the hub 160 are disposed on the axis C1 that extends along the extending direction of the image diagnosis catheter 100, and the outer tube 120 is held in a linear shape. In addition, since the axis C1 that extends along the extending direction of the image diagnosis catheter 100 extends in parallel to the tangent T of the outer contour line of the wound holder tube 200, the extending direction of the outer tube 120 exposed from the holder tube 200 is in a parallel positional relationship to the tangent T.

Due to the positional relationship in which the tangent T of the outer contour line of the wound holder tube 200 and the extending direction of the outer tube 120 exposed from the holder tube 200 are parallel to each other as described above, the catheter holder 10 prevents the outer tube 120 from being bent and prevents the inner shaft 130 accommodated in the outer tube 120 from being bent by holding the outer tube 120 at a fixed position.

The term "parallel" disclosed here merely expresses the state of a desired positional relationship to prevent the bending of the outer tube 120, and a holding shape for preventing the bending of the outer tube 120 by the catheter holder 10 is not necessarily limited to the positional relationship in which the outer tube 120 is parallel to the tangent line T. Therefore, a certain allowable range may be set in the positional relationship between the tangent T of the outer contour line of the wound holder tube 200 and the outer tube 120, which is derived when the outer tube 120 is held by the catheter holder 10. Specifically, in the holding shape of the outer tube 120 by the catheter holder 10, assuming that the tangent T is a reference axis, the gradient of the outer tube 120 relative to the reference axis is set, on the basis of the coupling portion between the opening 205a of the holder tube 200 and the relay connector 170 (the tip end of the relay connector 170 exposed from the opening 205a), to an appropriate holding range from a state in which the outer tube 120 is rotated by 5 degrees to the winding direction of the holder tube 200 to a state in which the outer tube 120 is rotated by 15 degrees to the direction that is opposite to the winding direction of the holder tube 200 while holding the outer tube 120 in a linear shape. The rotation angle of the outer tube 120 relative to the tangent T, which is defined as the appropriate holding range, is calculated as a minimum value that is required for allowing the catheter holder 10 to exert the function of holding the outer tube 120 in an appropriate state (preventing the bending tendency of the outer tube). For example, the description "5 degrees to the winding direction of the holder tube 200" means an angle at which the outer tube 120 and the holder tube 200 begin to have a new contact point, in addition to the existing contact point between the opening portion 205a of the holder tube 200 and the relay connector 170, and the outer tube 120, which is held in this state, may be sufficiently held in a linear shape. In addition, likewise, even when the angle is set to "15 degrees to the direction that is opposite to the winding direction side of the holder tube 200", the outer tube 120 may be sufficiently held in a linear shape. In addition, the plane on which the outer tube 120 is moved may be a plane defined by the holder tube 200, or a plane that is in a positional relationship of being perpendicular to the plane defined by the holder tube 200. In addition, when the image diagnosis catheter 100 is supported relative to the holder tube 200 via the support section 30 provided in the catheter holder 10, it is possible to prevent the load of the hub 160 or the unit connector 150 of the image diagnosis catheter 100 from being unintentionally applied to each part of the image diagnosis catheter 100, so that the image diagnosis catheter 100 can be held in a stable state.

In addition, as illustrated in FIG. 5, for example, when the outer tube 120 is disposed such that the extending direction of the outer tube 120 overlaps or is in parallel with the tangent T that is orthogonal to the normal N that passes through the winding center P1 of the holder tube 200, it is possible to more reliably prevent the outer tube 120 and the inner shaft 130 from being folded or bent. Therefore, it is more desirable to hold the outer tube 120 in the positional relationship as illustrated.

Figure 7A:
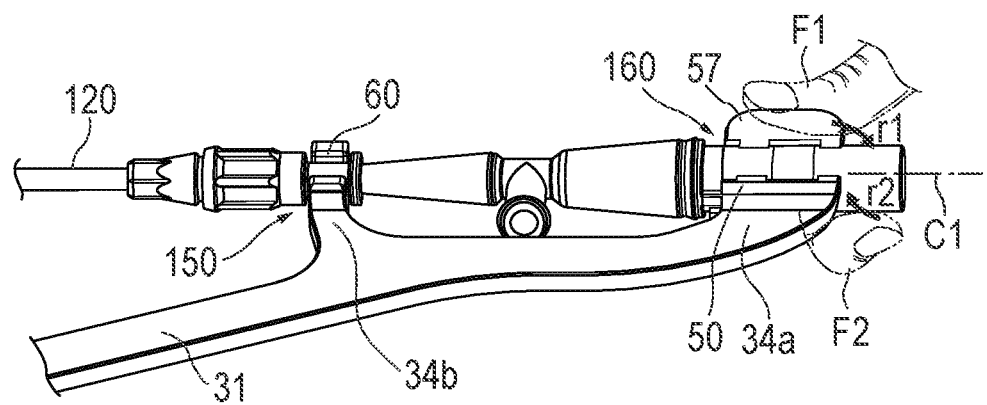
Figure 7B:
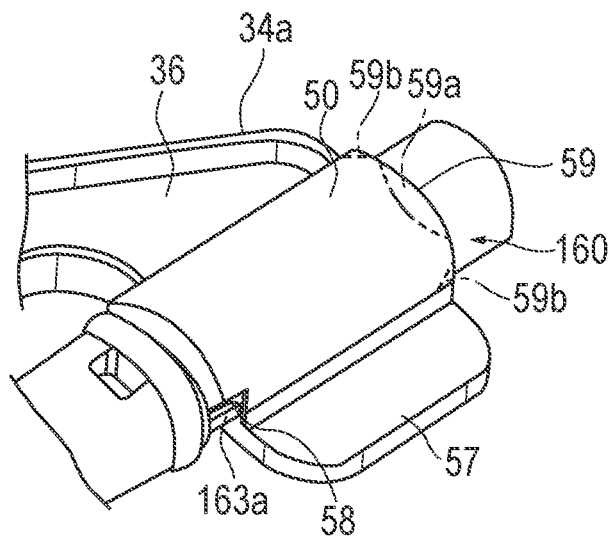

When releasing the holding of the image diagnosis catheter 100 by the catheter holder 10, as illustrated in FIG. 7A, an operation of releasing the fixing of the hub 160 by the hub-side fixing part 50 is performed.

The hub-side fixing part 50 is configured to release the fixing of the hub 160 by imparting force thereto in a direction of relatively separating the hub 160 therefrom. When releasing the fixing, pressing force is applied by hooking a finger F1 (e.g., the thumb), from the upper side, with the finger hooking portion 57 formed on the hub-side fixing part 160. At this time, when the vicinity of the base end of the hub 160 is lifted with another finger F2 (e.g., the index finger) from the lower side, the hub 160 may be easily separated from the hub-side fixing part 50. In addition, for example, when the hub 160 is twisted such that the finger hooking portion 57 is pushed down around the axis C1 by the finger F1 and the vicinity of the base end of the hub 160 is pushed up around the axis C1 by the finger F2 (see the arrows r1 and r2 in FIG. 7A), the hub 160 may be easily taken out from the first groove portion 51 of the hub-side fixing part 50, and the hub 160 taken out from the first groove portion 51 of the hub-side fixing part 50 may be held in a state of being pinched by the fingers F1 and F2.

In addition, in a case where the hub-side fixing part 50 is formed of an elastically deformable resin material or the like, the hub-side fixing part 50 may be configured to release the fixing of the hub 160 using the elastic deformation thereof. In addition, for example, in order to enable the hub-side fixing part 50 to be easily elastically deformed by the fingers or the like and to be easily hooked by the fingers, for example, a recessed groove 59*a* may be formed in an end 59 of the hub-side fixing part 50 or the like, or a tapered portion 59*b* may be formed on each part (see FIG. 7B).

The fixing of the unit connector 150 by the connector-side fixing part 60 may be released in conjunction with the operation of releasing the fixing of the hub 160 by the hub-side fixing part 50 and lifting the hub 160. As described above, since the connector-side fixing part 60 fixes the unit connector 150 with relatively low fixing force, it is not necessary to perform an operation such as twisting, which is required at the time of releasing the fixing by the hub-side fixing part 50, and the fixing by the connector-side fixing part 60 may be simply released by only the force (lifting force) applied to the unit connector 150 side when lifting the hub 160. In addition, since the second opening portion 62 of the connector-side fixing part 60 is opened in the same direction as the first opening portion 52 of the hub-side fixing part 50 (see FIG. 4B) and the lifting direction of the hub 160 and the lifting direction of the unit connector 150 coincide with each other, the image diagnosis catheter 100 may be held with the fingers by releasing the fixing of the hub 160 and lifting the hub 160. Therefore, immediately after the holding by the catheter holder 10 is released, it is possible to prevent the load of the hub 160, the unit connector 150, or the like from being unintentionally applied to each part of the image diagnosis catheter 100.

Next, the action of the base portion 33 provided in the support section 30 will be described with reference to FIGS. 8A and 8B.

Figure 8A:
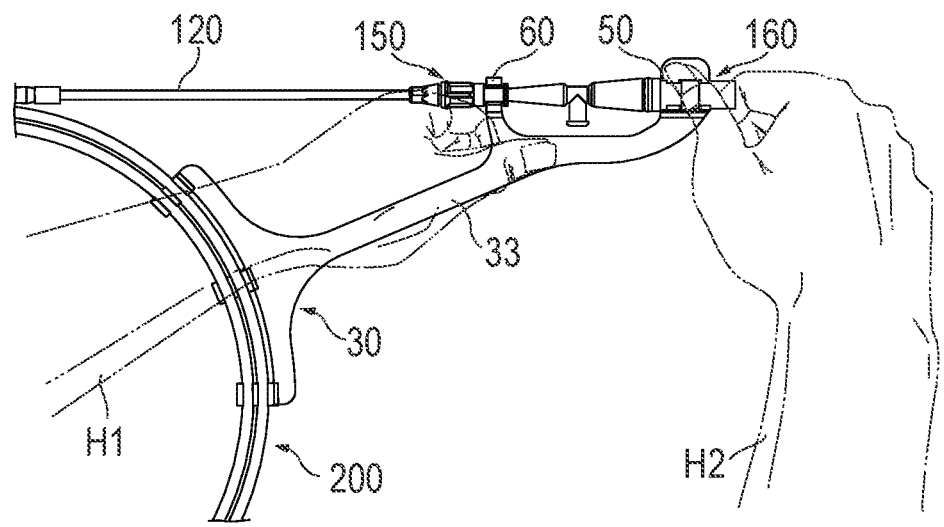
Figure 8B:
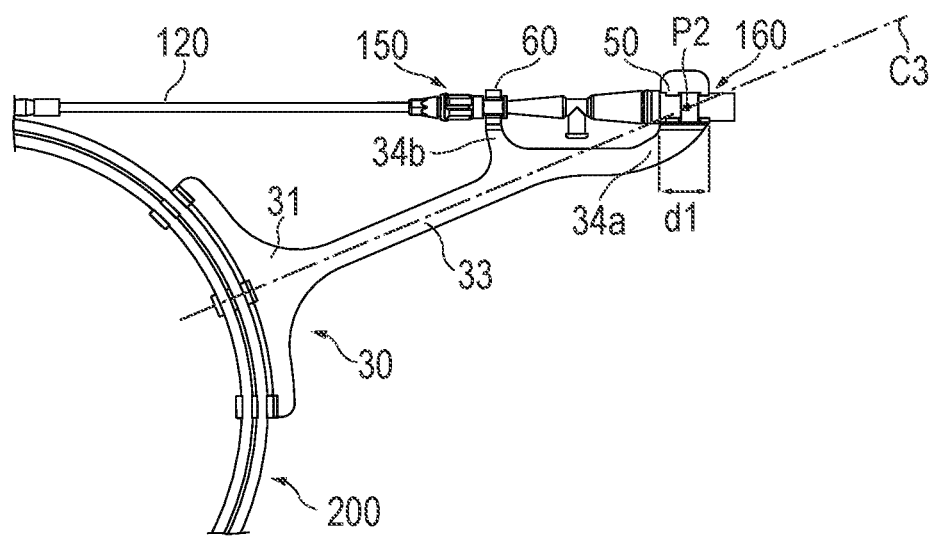

As illustrated in FIG. 8A, when releasing the fixing of the hub 160 by the hub-side fixing part 50, the base portion 33 provided in the support section 30 functions as a grip portion that may be gripped with one hand (e.g., the left hand) H1 of the operator. For example, the operator may efficiently release the fixing of the hub 160 by twisting the above-described hub-side fixing part 50 using the fingers of the other hand (e.g., the right hand) H2 while gripping and pushing the base portion 33 with the one hand.

At this time, when the portion of the hub-side fixing part 50, to which force is applied, is present on the extension line of the portion that is gripped by the one hand H1, the force applied from the one hand H1 side to press the base portion 33 acts to suppress the axial deflection of the hub-side fixing part 50. Therefore, it is possible to efficiently transmit the force in the twisting direction when performing twisting by the other hand H2. That is, when the rotation axis when twisting the hub-side fixing part 50 with the other hand H2 coincides with the rotation axis of the wrist of one hand H1 (the rotation axis upon pronation by radius and ulna), the motion of the other hand H2 upon twisting may be efficiently performed, and therefore the hub 160 may be easily taken out from the hub-side fixed part 50.

In consideration of the function described above, as illustrated in FIG. 8B, the base portion 33 provided in the support section 30 is formed to extend toward the hub-side fixing part 50 such that the extension line C3 of the extending direction thereof overlaps the portion P2 of the hub-side fixing part 50 to which force is applied when releasing the fixing of the hub 160. In addition, a portion of the hub-side fixing part 50, to which the greatest force is applied when releasing the fixing, is not uniquely determined since such a portion may be changed depending on the operator, the operating situation, or the like. Thus, in normal use, it is considered that the operator performs an operation of applying the greatest force on the center position in the extending direction of the hub-side fixed part 50 (an intermediate position of the length dl). Therefore, in the exemplary embodiment, the direction (extending direction) in which the base portion 33 extends is set such that the extension line C3 of the extending direction of the base portion 33 intersects the center position P2 in the extending direction of the hub-side fixing part 50.

As described above, according to the catheter holder 10 or the catheter set 1 according to the exemplary embodiment, it is possible to prevent bending tendency from occurring in the outer tube 120 due to the use of the holder tube 200. Therefore, it is possible to prevent the drive shaft 140 from being kinked when the image diagnosis catheter 100 is used. In addition, since the unit connector 150 or the hub 160 may be stably held while being supported with respect to the holder tube 200 until the use of the image diagnosis catheter 100 is initiated, it is possible to prevent load from being unintentionally applied to each part of the image diagnosis catheter 100 after the image diagnosis catheter 100 is taken out from the packaging container 300 and to prevent the occurrence of damage such as breakage in the drive shaft 140 during the operation of preparing use.

In addition, since the fixing section 40 includes the hub-side fixing part 50, which fixes the hub 160 to restrict the rotation of the hub 160 and releases the fixing of the hub 160 when force is applied thereto in a direction of relatively separating the hub 160 therefrom, and the connector-side fixing part 60, which fixes the unit connector 150 with smaller fixing force than the fixing force of the hub-side fixing part 50 for fixing the hub 160 and restricts the movement of the unit connector 150 in the direction away from the axial center of the outer tube 120, it is possible to prevent the rotation of the hub 160 by the hub-side fixing part 50, thereby preventing the entire image diagnosis catheter 100 from being rotated and displaced due to the rotation of the hub 160. In addition, since the unit connector 150 is relatively simply fixed by the connector-side fixing part 60, it is possible to prevent excessive force from being applied to the unit connector 150 when releasing the holding of the image diagnosis catheter 100. As a result, it is possible to hold the image diagnosis catheter 100 in a stable state and to prevent the inner shaft 130, which is inserted into the unit connector 150, from being kinked when the image diagnosis catheter 100 is removed.

In addition, since the support section 30 includes the base portion 33 formed to extend toward the hub-side fixing part 50 such that the extension line C3 in the extending direction overlaps the portion of the hub-side fixing part 50, to which force is applied when releasing the fixing of the hub 160, the force applied from one hand H1 side to press the base portion 33 acts to suppress the axial shaking of the hub-side fixing part 50. Therefore, when performing a twisting operation by the other hand H2, the force may be efficiently transmitted in the twisting direction, and as a result, it becomes possible to smoothly release the fixing by the hub-side fixing part 50.

In addition, since the hub-side fixing part 50 includes the first groove portion 51 capable of accommodating the hub 160, the first opening portion 52 that allows the hub 160 to be inserted into the first groove portion 51 therethrough, and the pull-out prevention portions 54 and 55, which prevent the hub 160 from being pulled out from the first groove portion 51, and the connector-side fixing part 60 includes the second groove portion 61 capable of accommodating the unit connector 150, and the second opening portion 62 that is opened to the same direction as the first opening portion 52 and allows the unit connector 150 to be inserted into the second groove portion 61, the fixing by the hub-side fixing part 50 and the connector-side fixing part 60 may be released when the operation of holding up the hub 160 is performed, and, after the operation of removing the hub 160 from the catheter holder 10 is performed, the hub 160 may be held as it is in a state of being gripped by the fingers. Then, since it is possible to prevent the load of the hub 160, the unit connector 150, or the like from being applied to each part of the image diagnosis catheter 100 after the removal of the hub, it is possible to prevent the inner shaft 130, which is inserted into the unit connector 150, from being kinked after the image diagnosis catheter 100 is removed and until the use thereof is initiated.

Next, modifications of the catheter holder 10 according to the above-described embodiment will be described. In addition, in the descriptions of the catheter holder 10, members that may be configured in the same manner as the above-described members or have the same functions as the above-described members will be given the same reference numerals, and the descriptions thereof will be omitted.

First Modification

Figure 9A:
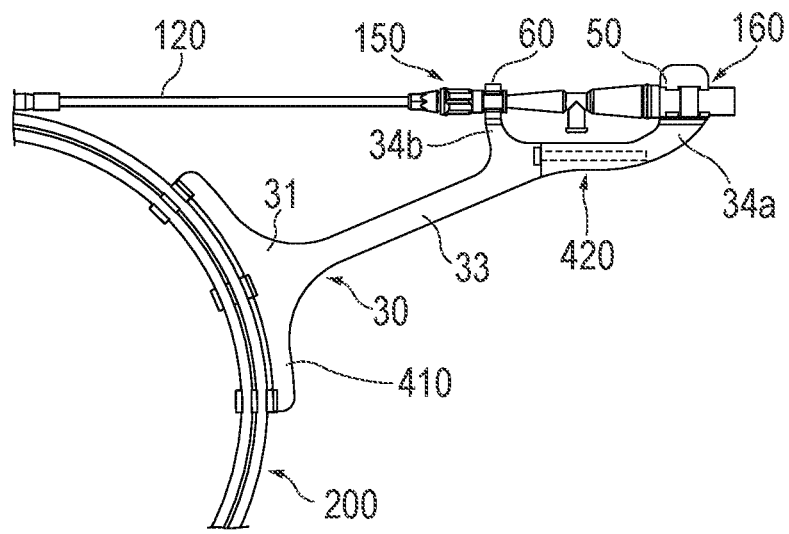
Figure 9B:
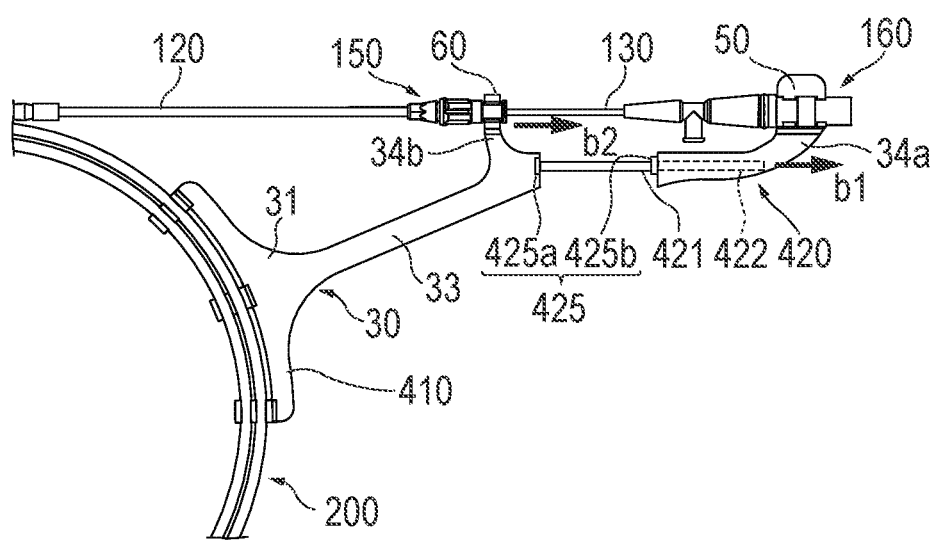

As illustrated in FIGS. 9A and 9B, a catheter holder 410 according to the first modification differs from the above-described catheter holder 10 in that the catheter holder 140 includes a length adjustment part 420 that makes the distance between the hub-side fixing part 50 and the connector-side fixing part 60 variable.

As illustrated in FIG. 9B, the length adjustment part 420 includes a slide guide portion 421, a slide guide accommodating portion 422 formed in the first branch portion 34a of the support section 30, and a stopper 425.

The slide guide portion 421 has a linear shape and functions as a guide when the hub-side fixing part 50 is moved toward or away from the connector-side fixing part 60. Before the distance between the hub-side fixing part 50 and the connector-side fixing part 60 is adjusted, the slide guide portion 421 is accommodated in the slide guide accommodating portion 422.

As indicated by the arrow b1 in FIG. 9B, when the hub-side fixing part 50 is moved away from the connector-side fixing part 60 along the slide guide 421, the distance between the hub-side fixing part 50 and the connector-side fixing part 60 is adjusted to be increased. In addition, at this time, when the hub-side fixing part 50 is moved in a state in which the hub 160 is fixed by the hub-side fixing part 50 and the unit connector 150 is fixed by the connector-side fixing part 60, the hub 160 is also pulled to the base end side along with the hub-side fixing part 50. When the hub 160 is pulled, the inner shaft 130 connected to the hub 160 is drawn out of the outer tube 120 and the unit connector 150 as indicated by the arrow b2 in FIG. 9B. In addition, the inner shaft 130 may be drawn out by moving the connector-side fixing part 60 away from the hub-side fixing part 50 along the slide guide 421.

The stopper 425 is provided in order to prevent the hub-side fixing part 50 and the connector-side fixing part 60 from being unintentionally moved by the slide guide 421.

The stopper 425 may be configured by a known snap mechanism, which is switchable between a locked state of restricting the movement of the hub-side fixing part 50 and the connector-side fixing part 60 and an unlocked state of allowing the movement of the hub-side fixing part 50 and the connector-side fixing part 60. In the illustrated example, the stopper 425 is configured by a fitting groove 425a and a convex portion 425b fittable into the fitting groove, which are configured to be mechanically coupled to and separated from each other. In addition, the stopper 425 may at least function to prevent the slide guide 421 from being unintentionally drawn out, and may be configured to restrict the movement by magnetic force or the like. In addition, for example, the stopper 425 may include a snap mechanism that may allow the user to know that the inner shaft 130 has been drawn out to the maximum extent via the feel of fingers.

As illustrated in FIG. 9A, when the slide guide 421 is configured to be accommodated in the first branch portion 34a of the support section 30, the slide guide 421 may be accommodated in a compact manner. However, the length of the slide guide 421 is limited within a range that does not exceed the length of the first branch portion 34a. For example, when it is desired to make the length of the slide guide 421 longer than the length of the first branch portion 34a, that is, when it is desired to increase the amount of drawing out the inner shaft 130, the slide guide 421 may be configured in a nested structure to be stretched in multiple stages.

With the catheter holder 410 according to the first modification, since it is possible to perform priming by stretching the inner shaft 130 in a state in which the image diagnosis catheter 100 is held by the corresponding catheter holder 410, the time and effort of removing the image diagnosis catheter 100 from the catheter holder 410 for priming may be omitted. In addition, since the catheter holder 410 may firmly hold the image diagnosis catheter 100 even during the priming, it is possible to prevent an unintentional load from being applied to each portion of the image diagnosis catheter 100 during the priming.

Second Modification

Figure 10:
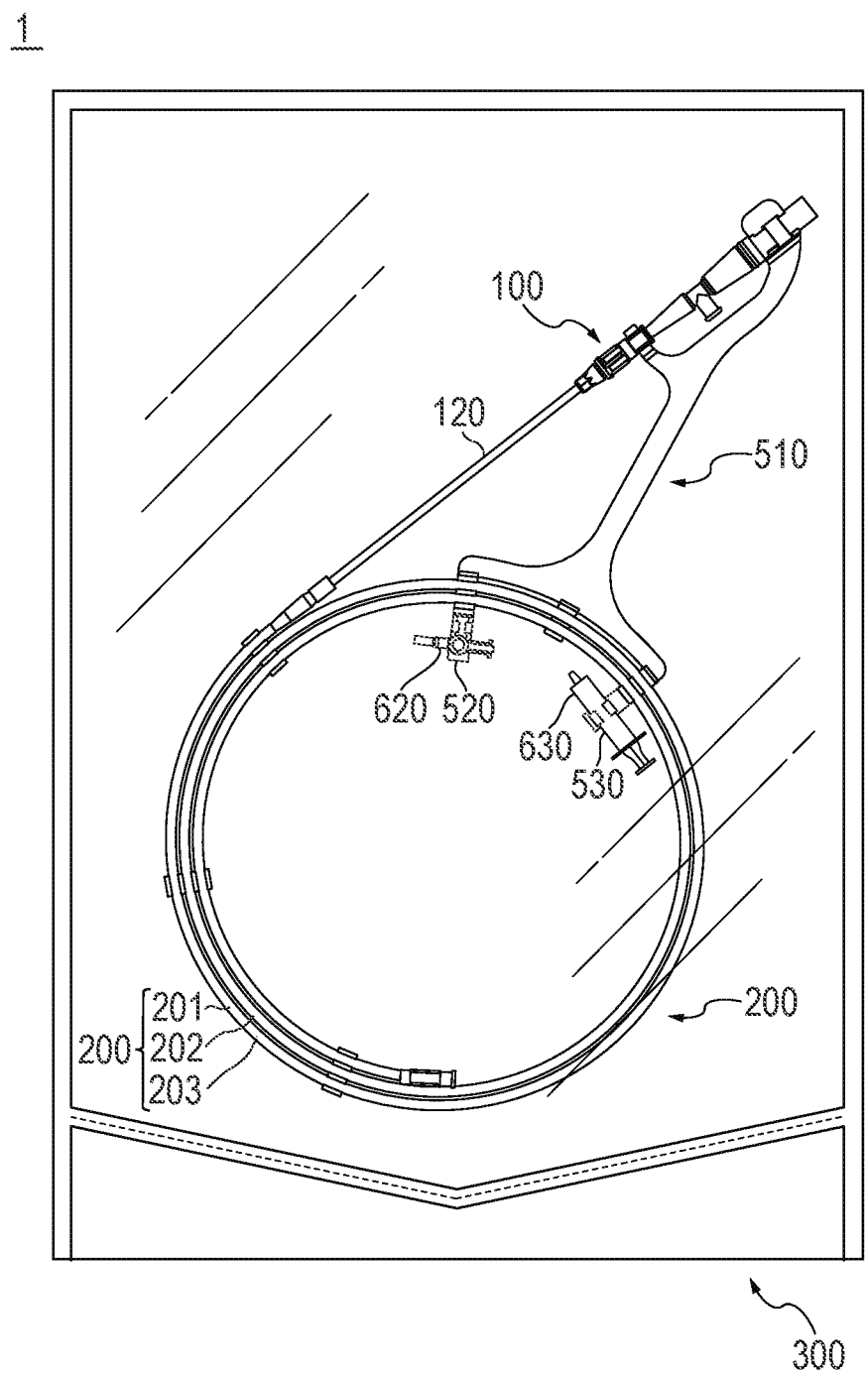
FIG. 10 is a plan view illustrating a catheter set including a catheter holder according to a second modification.
Figure 11:
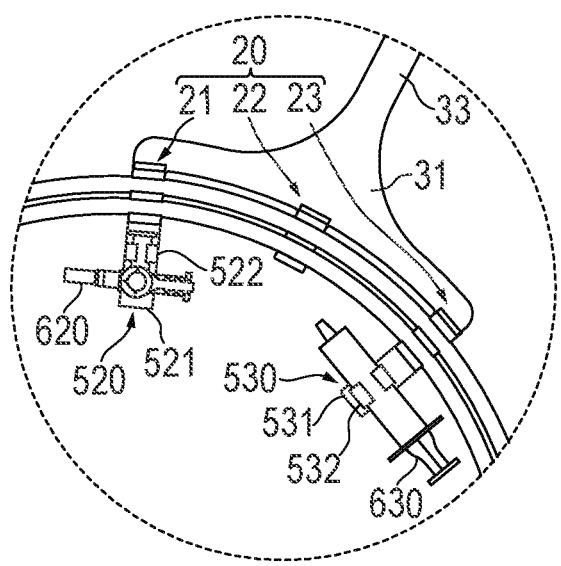
FIG. 11 is an enlarged view illustrating the important part of the catheter holder according to the second modification.

As illustrated in FIGS. 10 and 11, a catheter holder 510 according to the second modification differs from the catheter holder 10 described above in that the catheter holder 510 includes medical instrument holding parts 520 and 530 that detachably fix medical instruments 620 and 630, which are attached to the image diagnosis catheter 100.

The medical instrument holding part 520 provided in the catheter holder 510 is provided in order to hold a three-way stopcock 620, which is a medical instrument attached to the image diagnosis catheter 100. In addition, the medical instrument holding part 530 provided in the catheter holder 510 is provided to hold a syringe 630, which is a medical instrument attached to the image diagnosis catheter 100.

In addition, the medical instruments to be held by each of the medical instrument holding parts 520 and 530 are not limited to the three-way stopcock 620 and the syringe 630, but may be, for example, medical needles. In addition, the installation number of the medical instrument holding parts is not particularly limited, and may be appropriately changed.

Each of the medical instrument holding parts 520, 530 is provided on the attachment section 20 of the catheter holder 510. The medical instrument holding part 520 includes a support portion 521 that supports the three-way stopcock 620 and a fixing portion 522 that fixes the three-way stopcock 620 placed on the support portion 521. The medical instrument holding part 530 includes a support portion 531 that supports the syringe 630 and a fixing portion 532 that fixes the syringe 630 placed on the support portion 531.

Each of the support portions 521 and 531 may be configured as, for example, a simple plate-shaped member. In addition, each of the fixing portions 522 and 532 may be configured by a groove portion or the like that accommodates and fixes, for example, the three-way stopcock 620 or the syringe 630.

Each of the medical instrument holding parts 520 and 530 is disposed on the inner peripheral side of the wound holder tube 200 from the attachment section 20. Therefore, the three-way stopcock 620 and the syringe 630, which are fixed to the respective medical instrument holding parts 520 and 530, are disposed on the inner peripheral side of the wound holder tube 200. As illustrated in FIG. 10, since a relatively large space is present on the inner peripheral side of the wound holder tube 200, a useless space may be effectively used when medical instruments such as the three-way stopcock 620 and the syringe 630 are disposed at such positions.

With the catheter holder 510 according to the second modification, since medical instruments such as the three-way stopcock 620 and the syringe 630, which are attached to the image diagnosis catheter 100, may be held along with the image diagnosis catheter 100, excellent convenience may be obtained. In addition, since the space, which is present at the inner peripheral side of the wound holder tube 200, is effectively usable, despite additionally holding the three-way stopcock 620, and the syringe 630, and the like, it is possible to effectively suppress an increase in the area occupied by the catheter set 1 in the unused state.

In the foregoing, the catheter holder and the catheter set according to the present invention have been described with reference to exemplary embodiments and modifications. However, the present invention is not limited to only the configurations described in the exemplary embodiments.

For example, it is possible to provide a catheter holder in which the configuration according to the first modification and the configuration according to the second modification are combined.

For example, in the exemplary embodiments, it has been described that the catheter holder is configured to fix a hub and a connector unit of an image diagnosis catheter. However, the catheter holder may be configured to fix at least one of the hub and the connector unit. However, as described in the exemplary embodiment, when the catheter holder is configured to fix both the hub and the connector part, it is possible to maintain the held state of the image diagnosis catheter more suitably. In addition, it is possible to perform fixing at multiple positions in each of the hub and the connector part. In addition, the respective fixing structures of the attachment section, the hub-side fixing part, and the connector-side fixing part described in the exemplary embodiment, such as the snap-fit structure and the fitting structure, are exemplary, and may be appropriately changed so long as it is possible to fix the holder tube, the hub, the connector part, and the like.

For example, in the description of the exemplary embodiment, the inner shaft may be an inner tube (a tubular member) or a wire.

The configuration of each part of the image diagnosis catheter described in the exemplary embodiment is given by way of example, and the configuration of the image diagnosis catheter to be held is not particularly limited as long as it is configured to be held by the catheter holder. In addition, the connector and the hub to be fixed by the catheter holder do not strictly mean the respective constituent parts described with reference to the drawings, and generally include parts that correspond to the connector part and the hub that are provided in a constituent part, which is referred to as a handle operating part of the image diagnosis catheter, and a part that has the same function as each of the parts to be used in place of each of the parts.

Although an intravascular ultrasound diagnostic apparatus (IVUS) has been exemplified as an image diagnosis catheter that is an application target of the catheter holder, the image diagnosis catheter as the application target is not particularly limited so long as it is an image diagnosis catheter, which may cause various problems associated with winding and holding an outer tube. For example, the present invention may be applied to an optical coherence tomography (OCT), a hybrid type (dual type) image diagnosis catheter, which includes functions of both an intravascular ultrasonic diagnostic apparatus and an optical coherence tomography diagnostic apparatus and enables switching between these functions or simultaneous use of the functions, or an image diagnosis catheter using optical frequency domain imaging (OFDI). In addition, the application target of the catheter holder is not limited to only the image diagnosis catheter, but may be widely applied to all of catheters, which have the same problem as the image diagnosis catheter (e.g., the occurrence of kink due to the bending of the outer tube).

What is claimed is:

1. A catheter holder holding, in a predetermined state, a catheter having at least a portion accommodated within a wound holder tube, wherein the catheter holder comprises:
an attachment section configured to be attachable to the wound holder tube;
a support section formed to extend from the attachment section in a direction away from the wound holder tube; and
a fixing section provided on a second end side of the support section, which is opposite to a first end side of the support section on which the attachment section is provided, the fixing section being configured to hold an outer tube of the catheter exposed from an opening portion of the wound holder tube in a linear shape at a fixed position, the fixing section including a hub-side fixing part and a connector-side fixing part, wherein the hub-side fixing part includes a first groove portion configured to accommodate a hub of the catheter therein, and a first opening portion configured to allow the hub to be inserted into the first groove portion therethrough, the connector-side fixing part includes a second groove portion configured to accommodate a connector part of the catheter therein, and a second opening portion opened toward the same direction as the first opening portion and configured to allow the connector part to be inserted into the second groove portion therethrough, the opening portion of the holder tube faces the second groove portion of the connector-side fixing part, the second opening portion of the connector-side fixing part faces the first groove portion of the hub-side fixing part, and a first distance between the opening portion of the holder tube and the second groove portion is longer than a second distance between the second groove portion of the connector-side fixing part and the first groove portion of the hub-side fixing part.

2. The catheter holder according to claim 1, wherein the first distance is longer than a length of the support section between the attachment section and the fixing section.

3. The catheter holder according to claim 2, wherein the second distance is shorter than a length of the support section between the attachment section and the fixing section.

4. The catheter holder according to claim 1, wherein the second distance is shorter than a length of the support section between the attachment section and the fixing section.

5. The catheter holder according to claim 1, further comprising:

a length adjustment part that makes a distance between the hub-side fixing part and the connector-side fixing part variable.

6. The catheter holder according to claim 1, wherein the hub-side fixing part has a snap-fit structure including a pair of protruding pieces facing each other with a gap therebetween.

7. The catheter holder according to claim 1, further comprising:

a medical instrument holding part provided on the attachment section and configured to detachably fix a medical instrument attached to the catheter and to hold the medical instrument on an inner peripheral side of the wound holder tube.

8. A catheter holder according to claim 1, wherein the second end side of the support section bifurcated into a first branch portion and a second branch portion.

9. A catheter holder according to claim 8, wherein the first branch portion extends toward the hub-side fixing part and the second branch portion extends toward the connector-side fixing part.

10. A catheter holder according to claim 8, wherein a concave portion is provided between the first branch portion and the second branch portion.

* * * * *